United States Patent
Peters et al.

(10) Patent No.: US 10,858,623 B2
(45) Date of Patent: Dec. 8, 2020

(54) REMOVAL OF MICROORGANISMS FROM CELL CULTURE MEDIA

(71) Applicant: EMD Millipore Corporation, Burlington, MA (US)

(72) Inventors: Antoni Peters, Fitchburg, MA (US); Philip M. Goddard, Merrimack, NH (US)

(73) Assignee: EMD Millipore Corporation, Burlington, MA (US)

( * ) Notice: Subject to any disclaimer, the term of this patent is extended or adjusted under 35 U.S.C. 154(b) by 707 days.

(21) Appl. No.: 14/870,519

(22) Filed: Sep. 30, 2015

(65) Prior Publication Data

US 2016/0177252 A1    Jun. 23, 2016

Related U.S. Application Data

(60) Provisional application No. 62/095,259, filed on Dec. 22, 2014.

(51) Int. Cl.
| | | |
|---|---|---|
| *C12M 1/12* | (2006.01) | |
| *B01D 71/82* | (2006.01) | |
| *B01D 71/68* | (2006.01) | |
| *B01D 67/00* | (2006.01) | |

(52) U.S. Cl.
CPC .......... *C12M 37/02* (2013.01); *B01D 67/009* (2013.01); *B01D 67/0093* (2013.01); *B01D 71/68* (2013.01); *B01D 71/82* (2013.01); *B01D 2323/30* (2013.01); *B01D 2323/36* (2013.01); *B01D 2323/40* (2013.01); *B01D 2325/20* (2013.01)

(58) Field of Classification Search
CPC ............ B01D 2323/30; B01D 2325/36; B01D 2323/02; B01D 67/0006; B01D 67/0088; B01D 67/0093
See application file for complete search history.

(56) References Cited

U.S. PATENT DOCUMENTS

| | | | |
|---|---|---|---|
| 3,520,804 A | 7/1970 | Hoke | |
| 4,196,065 A * | 4/1980 | Gaussens | ............ A61M 31/002 239/34 |

(Continued)

FOREIGN PATENT DOCUMENTS

| | | |
|---|---|---|
| CN | 1035928 C | 9/1997 |
| CN | 101637704 A | 2/2010 |

(Continued)

OTHER PUBLICATIONS

Zhou et al., High Throughput Synthesis and Screening of New Protein Resistant Surfaces for Membrane Filtration, 56 AIChE J., 1932, 1932-1945 (2010). (Year: 2010).*

(Continued)

*Primary Examiner* — Krishnan S Menon
*Assistant Examiner* — Brad Gordon
(74) *Attorney, Agent, or Firm* — EMD Millipore Corporation

(57) ABSTRACT

Compositions and methods are provided for removing viral contaminants from a chemically defined cell culture medium. Compositions provided herein are resistant to or exhibit reduced fouling by one or more components in a chemically defined cell culture medium.

3 Claims, 13 Drawing Sheets

(56) References Cited

U.S. PATENT DOCUMENTS

| | | | |
|---|---|---|---|
| 4,288,467 A * | 9/1981 | Machi | B01D 67/0093 264/413 |
| 4,522,913 A * | 6/1985 | Kanno | C07C 69/54 430/285.1 |
| 4,618,533 A | 10/1986 | Steuck | |
| 4,695,592 A * | 9/1987 | Itoh | B01D 67/0088 210/490 |
| 4,876,289 A | 10/1989 | Itoh et al. | |
| 5,209,849 A * | 5/1993 | Hu | B01D 67/0093 210/490 |
| 5,746,916 A * | 5/1998 | Kamo | B01D 67/0027 210/500.23 |
| 5,863,650 A | 1/1999 | Healy et al. | |
| 5,869,174 A * | 2/1999 | Wang | B01D 67/0011 210/500.41 |
| 5,906,742 A * | 5/1999 | Wang | B01D 67/0011 210/321.6 |
| 6,083,393 A | 7/2000 | Wu et al. | |
| 2011/0017654 A1 * | 1/2011 | Ueno | B01D 63/02 210/321.6 |
| 2011/0253621 A1 * | 10/2011 | Kim | B01D 65/08 210/500.39 |
| 2012/0024787 A1 | 2/2012 | Charkoudian et al. | |
| 2012/0048799 A1 | 3/2012 | Na et al. | |
| 2012/0076934 A1 | 3/2012 | Tkacik et al. | |
| 2012/0288630 A1 | 11/2012 | Charkoudian et al. | |
| 2013/0344535 A1 | 12/2013 | Mundt et al. | |

FOREIGN PATENT DOCUMENTS

| | | |
|---|---|---|
| CN | 101898432 A | 12/2010 |
| EP | 0911073 A1 | 4/1999 |
| JP | S62-163703 A | 7/1987 |
| JP | 2004-532724 A | 10/2004 |
| KR | 2007-0120126 A | 12/2007 |
| WO | 2002/087734 A1 | 11/2002 |
| WO | 03/103814 A1 | 12/2003 |
| WO | 2006/095595 A1 | 9/2006 |
| WO | 2013/192009 A1 | 12/2013 |

OTHER PUBLICATIONS

Folmsbee et al., "Retention of Highly Penetrative A. Laidlawii Mycoplasma Cells", Using a 0.1-µm-Rated Membrane Filter at Elevated Pressure with an Elevated Challenge Concentration, BioProcess International, vol. 10, No. 5, May 2012, pp. 60-62.

Liu et al., "Development and Qualification of a Novel Virus Removal Filter for Cell Culture Applications", Biotechnology Progress, vol. 16, Issue 3, 2000, pp. 425-434.

Reine et al., "Photoinitiated Polymerization onto Cotton", Copolymerization of Acrylamide Monomers with Cotton, Textile Research Journal vol. 42, No. 11, Nov. 1973, pp. 638-641.

Zydney et al., "Bioprocess Membrane Technology", Journal of Membrane Science, vol. 297, 2007, pp. 16-50.

International Search Report and Written Opinion for PCT Patent Application No. PCT/US2015/053135, dated Jan. 27, 2016, 14 pages.

* cited by examiner

REMOVAL OF MICROORGANISMS FROM CELL CULTURE MEDIA

Related Applications

The present application claims the benefit of priority of U.S. Provisional Application No. 62/095,259 filed on Dec. 22, 2014. The entire teachings of the above are incorporated herein by reference.

FIELD

Embodiments disclosed herein relate to compositions and methods for removing microorganisms, including viruses, from cell culture media.

BACKGROUND

Conventional processes for protein production typically involve cell culture methods, e.g., culturing either mammalian or bacterial cell lines recombinantly engineered to produce the protein of interest (e.g., a monoclonal antibody) in a bioreactor using a chemically defined cell culture media. Reduction of bioreactor contamination by microorganisms such as bacteria, fungi, mycoplasma and viruses is an important consideration for the biopharmaceutical industry, especially, when the protein of interest is intended for therapeutic use.

Among the microorganisms, bacteria, fungi and mycoplasma can typically be removed by filtering the cell culture media through appropriate filters. For example, microfiltration membranes with 0.2 um nominal pore size ratings are considered appropriate for the removal of bacteria of genus *Brevendumonas diminuta*. Membranes with 0.1 um nominal pore size ratings are considered suitable for the removal of mycoplasma, principally of the genus *Acholeplasma laidlawii*. See, e.g., Folmsbee and Moussorakis, BioProcess International, Vol. 10, No. 5, 2012, pp. 60-62 (May 2012). Further, a membrane with nominal pore size rating of 20 nm is considered suitable to effect a minimum 4 log reduction in parvovirus or parovirus-like particles, which represent the smallest of viruses.

It is considered challenging to generate membranes with pore size ratings for virus removal, as reducing the pore size rating such that to retain virus, can result in partial or complete constriction of membrane pores, thereby to significantly reduce membrane permeability to undesirable levels. Incidentally, there are currently no commercially available membrane filters that are specifically designed for removal of viruses in the upstream process and which are effective in doing so.

One of the reasons that virus barrier filters that are typically used downstream of the cell culture step are not effective for removal of viruses upstream is due to notable differences between the upstream and downstream compositions. For example, in case of the upstream process, there are no cells or expressed proteins in the cell culture media. However, there are nutrients, lipids, amino acids and other components (e.g., Pluronic F68 which provides hydrodynamic cell protection), all of which are required for cell growth and viability. In contrast, in case of the downstream process, the cell culture media contains cells, cellular debris, host cell proteins as well as the protein being expressed. Therefore, in case of the downstream process, the cell culture media is often subjected to a number of purification steps in order to remove undesirable virus filter foulants, prior to being subjected to a virus filtration step.

Notably, because of the differences in the nature of the compositions requiring purification, e.g., a chemically defined cell culture media in case of upstream virus removal versus a cell culture media containing an expressed recombinant protein in case of downstream virus removal, the membrane filters that are typically used downstream for virus removal do not tend to work too well for the same purpose when used upstream. See, e.g., Zydney et al., Journal of Membrane Science, 297: 16-50 (2007).

There have been attempts to develop virus barrier filters that can be specifically used upstream to filter a chemically defined cell culture medium. See, for example, Biotechnol Prog., 16:425-434 (2000), which discusses virus retention results obtained with a variety of filters. As demonstrated in this paper, a regenerated cellulose filter showed the highest flux of any filter that was tested and also exhibited high virus retention; however, such a membrane is not suitable for sterilization by steaming in place or by gamma radiation, sterilization methods typically employed in the industry today. Although, this paper also described a PES filter, this filter was considered generally undesirable for use as a virus barrier filter for upstream use due to its low flux.

Further, U.S. Publication No. 20130344535 discusses filtration of a chemically defined cell culture media to remove virus contaminants by using a filtration time of longer than 24 hours and by using a filter of certain porosity.

SUMMARY

Embodiments disclosed herein provide novel compositions for removing microorganisms, especially viruses, from a chemically defined medium used for culturing cells expressing a protein of interest. Accordingly, such compositions can be used prior to the step of transferring a cell culture medium into a bioreactor for culturing cells, e.g., mammalian cells expressing a recombinant protein of interest.

The compositions described herein are based on surface modifications of membranes resulting in membranes which exhibit reduced fouling by one or more components in a chemically defined cell culture medium, when such medium is filtered through the membrane.

In some embodiments, compositions described herein are directed to a porous membrane having a surface modified with a polymer comprising randomly arranged and cross-linked monomers of diacetone acrylamide and one or more non-acrylamide cross-linkable monomers.

In various embodiments, the polymer comprising randomly arranged and crosslinked monomers of diacetone acrylamide and one or more non-acrylamide cross-linkable monomers is directly coated onto the surface of a porous membrane using an energy source. Exemplary energy sources include, but are not limited to, heat, electron beam, ultraviolet light and gamma radiation.

Exemplary non-acrylamide cross-linkable monomers include, but are not limited to, polyethylene glycol diacrylate (PEGDA), glycerol diacrylate, polyethylene glycol dimethacrylate, ethoxylated trimethylol propane triacrylate, tetraethylene glycol diacrylate and tetraethylene glycol dimethacrylate. In a particular embodiment, a non-acrylamide cross-linkable monomer is PEGDA.

In some embodiments, the porous membrane is an asymmetric membrane such as, for example, a polyethersulfone (PES) membrane, Also provided herein are methods of using the described modified porous membranes for removing a virus contaminant from a chemically defined cell culture medium, e.g., by filtering a chemically defined cell culture medium through the modified membrane.

In some embodiments, a porous asymmetric PES membrane modified with a polymer comprising the following structure:

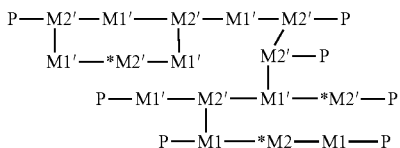

wherein,

M1 is neutral DACm monomer: $H_2C=CH-C(O)-NH-C(CH_3)_2-CH_2-C(O)-CH_3$;

M2 is neutral PEGDA monomer: $H_2C=CH-C(O)-O-(CH_2-CH_2-O)_n-C(O)-CH=CH_2$;

Mr is radicalized DACm monomer: $*H_2C-CH-C(O)-NH-C(CH_3)_2-CH_2-C(O)-CH_3$;

M2' is the radicalized PEGDA monomer: $*H_2C-CH-C(O)-O-(CH_2-CH_2-O)_n-C(O)-CH-CH_2*$;

P refers to a random polymer network; n=6, 7, 8, 9, 10, 11; and the symbol "*" refers to an alkenyl radical.

In some embodiments, a porous asymmetric PES membrane modified with a polymer comprising the following structure:

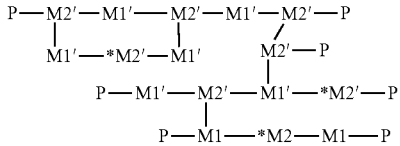

wherein,

M1 and M2 refer to a neutral PEGDA monomer: $H_2C=CH-C(O)-O-(CH_2-CH_2-O)_n-C(O)-CH=CH_2$;

M1 and M2' refer to a radicalized PEGDA monomer: $*H_2C-CH-C(O)-O-(CH_2-CH_2-O)_n-C(O)-CH-CH_2*$;

P refers to a random polymer network;

n=6, 7, 8, 9, 10, 11; and the symbol "*" refers to an alkenyl radical.

In some embodiments, a method of removing one or more viral contaminants from a chemically defined cell culture medium is provided, where the method comprises the steps of: (a) providing a chemically defined cell culture medium; and (b) filtering the chemically defined cell culture medium through a porous membrane prior to or during transfer of medium into a bioreactor, where the membrane has a surface modified with a polymer comprising randomly arranged and crosslinked monomers of diacetone acrylamide and one or more non-acrylamide cross-linkable monomers, where the level of one or more viral contaminants in the chemically defined cell culture medium inside the bioreactor is lower than the level prior to filtering the medium through the modified membrane.

In some embodiments, the modified membranes described herein are incorporated into a device. Exemplary device formats include, but are not limited to, a disc, a pleated cartridge, a spirally wound cartridge and a multi-plate flat sheet.

In some embodiments, the chemically defined cell culture medium is a commercially available chemically defined cell culture medium such as, for example, Lonza Power CHO, CD Opti CHO, EMD Millipore Cellvento CHO 100 and Cellvento CHO 200.

The level of one or more viral contaminants in a chemically defined cell culture medium is reduced by at least 1 Login reduction value (LRV) or at least 4 Login reduction value (LRV) or at least 6 Login reduction value (LRV), using the modified membranes described herein.

In various embodiments, a chemically defined cell culture medium is filtered through a modified membrane described herein for a period of less than 24 hours. In some embodiments, filtration is conducted at a pH ranging from 4 to 8 and/or at a temperature ranging from 20° C. to 25° C.

Also provided herein are methods of reducing the fouling of a virus retentive membrane by one or more components in a chemically defined cell culture medium, the method comprising the steps of: (a) providing a virus retentive membrane; and (b) modifying the membrane with a polymer comprising randomly arranged and crosslinked monomers of diacetone acrylamide and one or more non-acrylamide cross-linkable monomers, where the fouling of the modified membrane by one or more components in a chemically defined cell culture medium is reduced relative to an unmodified membrane.

In some embodiments, a virus retentive membrane is based on a PES membrane, a PVDF membrane, a cellulosic membrane or a nylon membrane.

In some embodiments, a non-acrylamide cross-linkable monomer is polyethylene glycol diacrylate (PEGDA).

DETAILED DESCRIPTION

Figure 1:
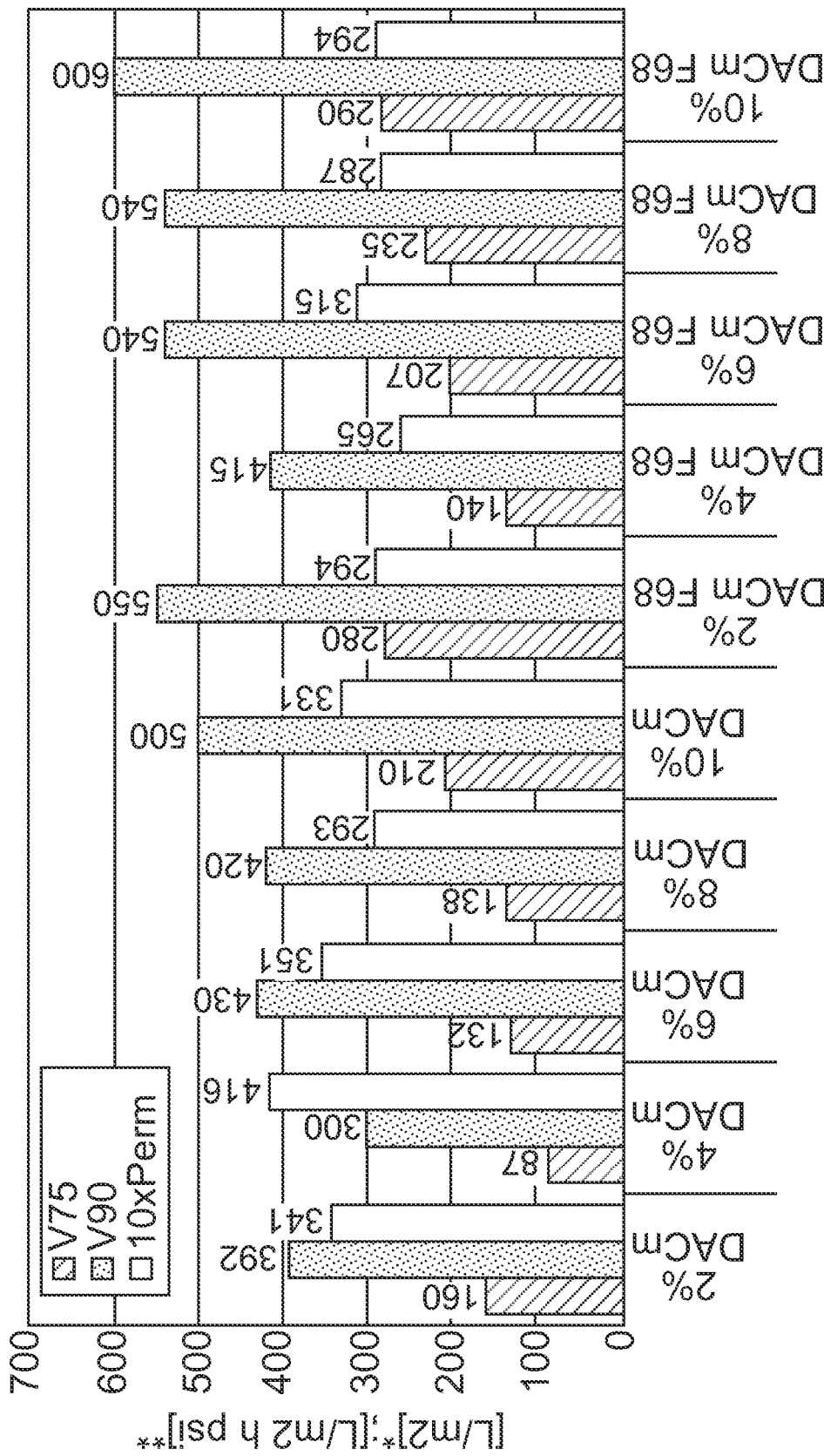
FIG. 1 is a bar graph depicting throughput performance results for a diacetone acrylamide (DACm) homopolymer modified PES membrane with and without Pluronic F68 exposure using a CHO cell culture media as a feedstream. The first five data sets represent membrane performance of membranes modified using different percentages of a DACm solution (2%, 4%, 6%, 8% and 10%), as measured by V75 (L/m$^2$), V90 (L/m$^2$) and 10× permeability (L/m$^2$ h psi); and the next five data sets represent membrane performance of the same membranes with F68 exposure, also as measured by V75 (L/m$^2$), V90 (L/m$^2$) and 10× permeability (L/m$^2$ h psi).

The embodiments described herein relate to compositions and methods for removing a microorganism, e.g., a virus contaminant, from a chemically defined cell culture media, where the compositions exhibit reduced fouling by components of chemically defined cell culture media.

In particular, the embodiments described herein provide compositions and methods which employ a porous membrane having a surface modified with a polymer comprising randomly arranged and crosslinked monomers of diacetone acrylamide and one or more non-acrylamide cross-linkable monomers such as, for example, polyethylene glycol diacrylates.

Also provided herein are methods of making virus barrier membranes resistant to fouling by one or more components of chemically defined cell culture media by modifying the surface of such membranes with a polymer comprising randomly arranged and crosslinked monomers of diacetone acrylamide and one or more non-acrylamide cross-linkable monomers (e.g., PEGDA).

In order that the embodiments disclosed herein may be more readily understood, certain terms are first defined. Additional definitions are set forth throughout the detailed description.

I. Definitions

The term "chemically defined cell culture media," refers to a growth medium suitable for the cell culture of mammalian cells (e.g., human or animal cells), in which all of the chemical components are known. Examples of commercially available chemically defined cell culture media include, but are not limited to, Lonza Power CHO, CD Opti CHO, EMD Millipore Cellvento CHO 100 and Cellvento CHO 200.

It has been demonstrated that hydrodynamic cell protecting amphiphilic compounds, in particular Pluronic F68 (BASF) and/or Poloxamer 188 (ICI) are the main media component(s) responsible for membrane filter fouling in various commercially available chemically defined cell culture media. Because one or more of these components have been observed to cause membrane fouling, they significantly reduce the effectiveness of membrane filters to remove virus contaminants.

The embodiments described herein relate to membrane compositions which are effective in removing virus contaminants even in the presence of media components that are known to foul membranes, e.g., Pluronic F68.

The terms "contaminant," "impurity," and "debris," as used interchangeably herein, refer to an undesirable or objectionable microorganism which may be present in a chemically defined cell culture media. In a particular embodiment, such a microorganism is a virus or a virus particle. In various embodiments, compositions and methods described herein are intended to effectively remove such virus contaminants from a chemically defined cell culture media by filtering the chemically defined cell culture media through a membrane filter that is modified to reduce or eliminate fouling by certain components that are typically present in commercially available chemically defined cell culture media. Accordingly, the embodiments described herein provide compositions that retain their virus retention capacity and membrane throughput even when exposed to components that typically foul most virus retention membranes.

Viral contaminants or potential viral contaminants that may be removed using the compositions and methods described herein include a member of the families of Orthomyxoviridae, Arenaviridae, Paramyxoviridae, Rhabdoviridae, Coronaviridae, Flaviviridae, Picornaviridae, Togaviridae, Arteriviridae, RetParvoviridae, Bunyaviridae, Caliciviridae, Retroviridae, Reoviridae, Circoviridae, Adenoviridae, Poxviridae, Herpesviridae, Iridoviridae or Reoviridae. More specifically, the viral contaminant may be any one of canine Parvoviridae (CPV), minute virus of mice (MVM), Cache Valley virus, Bunyamwera virus, Northway encephalitis virus, Influenza NB virus, Junin virus, Parainfluenza virus 1/2/3, Simian virus 5, Mumps virus, Bovine respiratory syncytial virus, Sendai virus, Newcastle disease virus, Pneumonia virus of mice, vesicular stomatitis virus, Rabies virus, Bovine coronavirus, Murine hepatitis virus, Yellow fever virus, West Nile virus, Dengue virus, Tick borne encephalitis virus, St. Louis encephalitis virus, Vesivirus 2117, Encephalomyocarditis virus, Coxsackie virus B-3, Theiler's mouse encephalitis virus, Foot and mouth disease virus, Bovine enterovirus, Porcine enterovirus, Semliki Forest virus, Sindbis virus, Rubella virus, Japanese encephalitis virus, Eastern equine encephalitis virus, Porcine reproductive and respiratory syndrome virus, Foamy virus, Reovirus 1/2/3, Avian reovirus, Rotavirus, Porcine circovirus 1, Adenovirus, Pseudorabies virus, Murine gammaherpes 68, Herpes simplex virus 1, Frog virus 3, minute virus of mice-cutter (MVMc), bluetongue virus (BTV), Epizootic haemorrhagic disease virus (EHDV), bovine viral diarrhea virus (BVDV), porcine parvovirus (PPV), encephalomyocarditis virus (EMCV), Reovirus 3, and murine leukemia virus (MuLV), Hepatitis A, polio, or Parvoviridae B19.

The term "log reduction value" (LRV), as used herein, refers to a measure of a membrane's efficiency to retain a particle, e.g., a virus contaminant, defined as the logarithm (base 10) of the ratio of the particle count in a feed stream (e.g., a chemically defined cell culture medium) to the particle count in the virus filter membrane permeate. In various embodiments described herein, the membrane filters achieve at least a 1 $Log_{10}$ reduction value (LRV) for a viral contaminant, or at least a 2 $Log_{10}$ reduction value (LRV) for a viral contaminant, or at least a 3 $Log_{10}$ reduction value (LRV) for a viral contaminant, or at least a 4 $Log_{10}$ reduction value (LRV) for a viral contaminant, or at least a 5 $Log_{10}$ reduction value (LRV) for a viral contaminant, or at least a 6 $Log_{10}$ reduction value for viral contaminant, or at least a 7 $Log_{10}$ reduction value for viral contaminant, or at least a 8 $Log_{10}$ reduction value for viral contaminant, preferably at least a 4 $Log_{10}$ reduction value (LRV) for a viral contaminant.

The term "fouling" refers to a process where solute or particles deposit onto a membrane surface or into membrane pores in a way that degrades the membrane's performance, such as, decline in membrane flux and/or throughput. In various embodiments described herein, virus membrane filters are provided which are resistant to or exhibit reduced fouling by one or more components present in chemically defined cell culture medium. Further, methods provided herein can be used for making compositions that are resistant to or exhibit reduced fouling by one or more components of a chemically defined cell culture medium.

The term "flux" or "membrane flux" (J), as used herein, refers to the instantaneous rate of permeate flow, which is generally variable in nature (expressed as the volume or weight of a permeate solution passing through the virus filtration membrane per unit of effective filtration area (EFA) per unit time, e.g. $L/(m^2 \times hr)$, or $g/(m^2\ hr)$, or $Kg/(m^2\ hr)$).

The term "initial flux" or "initial membrane flux" (Jo), as used herein, refers to the rate of permeate flow, which is usually constant in nature, when the permeate stream consists of a non-plugging fluid (i.e., water or a solution that contains no membrane fouling components).

The term "flux decay" or "membrane flux decay" (J/Jo), as used herein, refers to the ratio of the instantaneous membrane flux in a plugging permeate stream to the initial flux or the flux determined by passing a non-plugging permeate stream through the filter or membrane. It is often represented as a percentage, i.e., (J/Jo) %.

The term, "flux decay curve" refers to the curve generated when the flux decay (J/Jo) is plotted versus time (t), or versus volume (v) or versus mass (m) of filtrate collected, or preferably, versus volume (v) or versus mass (m) of filtrate collected per unit of effective filtration area (i.e., (J/Jo) % vs L/m$^2$, or (J/Jo) % vs Kg/m$^2$).

The term "throughput performance", refers herein to the quantity of filtrate that can be recovered per unit area of effective filtration area before the flux drops to 25%, or to 10%, of the initial flux (flux determined for a non-plugging stream).

The term "batch filtration," refers herein to a filtration process where a specific amount or volume of a chemically defined medium is filtered through a membrane filter in one batch to complete the filtration process, before the filtered media is transferred to or used in the next step in a process.

The term "continuous filtration" or "in line filtration" refers to a filtration process, wherein the specific amount or volume of a chemically defined cell culture medium is filtered through a membrane filter continuously and where the filtered medium is transferred to or may be used in the next step in the process as it is being filtered.

All embodiments described herein may be performed using batch or continuous filtration.

The term "solid support," as used herein, generally refers to any material which is modified with a polymer comprising randomly arranged and crosslinked monomers of diacetone acrylamide and one or more non-acrylamide crosslinkable monomers. An exemplary non-acrylamide crosslinkable monomer is polyethylene glycol diacrylate (PEGDA).

Examples of solid support formats used in the methods and compositions described herein include, but are not limited to, membranes and monoliths. In a particular embodiment, the solid support is a porous membrane whose surface is modified as described herein. Exemplary membranes include porous asymmetric membranes, e.g., a polyethersulfone membrane (PES), such as membranes made using process described in U.S. Patent Publication No. 20120076934.

As used herein, the term "surface" refers to entire surface area of a porous media or membrane, including external surfaces and the internal surface of the porous media or membrane. The term "external surface" means a surface that is exposed to view. The term "internal surface" is intended to denote the internal surface of a porous network, i.e., the interstitial area, of a porous media or membrane.

As used herein, the term "polymer" refers to a polymer made from at least two crosslinked monomers having reactive sites, where the monomers are randomly arranged and can take part in a polymerization reaction and where at least one monomer is diacetone acrylamide. In some embodiments, a polymer comprises diacetone and at least one or more non-acrylamide cross-linkable monomers such as, for example, polyethylene glycol diacrylate (PEGDA).

A monofunctional monomer is one that has a single unsaturated functional group. Polyfunctional monomers are molecules which have more than one unsaturated functional group.

The term "virus filter" or "virus retention filter" or "viral retention filter" or "virus barrier filter" refers to a membrane or media that retains viruses or virus-like particles in order to provide virus removal or virus clearance during upstream use (i.e., filtering a cell culture media prior to contacting with cells) or downstream use (i.e., filtering a cell culture media containing a recombinantly expressed protein). Examples of commercially available virus retention filters include Viresolve® Pro, Viresolve® NFP and Virosolve® NFR, which function primarily via a size exclusion mechansim. The embodiments described herein relate to virus barrier filters which are intended for upstream use and are positioned upstream of a bioreactor used for culturing cells expressing a protein of interest. Such virus barrier filters are modified such that they are resistant to or exhibit reduced fouling by one or more components of a chemically defined cell culture medium.

The term "feed" or "feedstream", as used interchangeably herein, refers to a solution or mixture that is to be subject to a filtration process, e.g., a chemically defined cell culture medium.

The term "filtrate" or "permeate," as used interchangeably herein, refers to the solution that crosses a filter or membrane as well as the solution that has crossed a filter or membrane.

The term "retentate," as used herein, refers to the component of the solution that is retained and does not cross a filter or membrane as well as that which has not crossed a filter or membrane.

The term "bioreactor," as used herein, refers to any manufactured or engineered device or system that supports a biologically active environment. In some instances, a bioreactor is a vessel in which a cell culture process is carried out that involves organisms or biochemically active substances derived from such organisms. Such a process may be either aerobic or anaerobic. In some embodiments, a bioreactor ranges in size from liters to cubic meters, and is made of stainless steel. In some embodiments, a bioreactor is made of a material other than steel and is disposable or single-use. It is contemplated that the total volume of a bioreactor may be any volume ranging from 100 mL to up to 10,000 Liters or more, depending on a particular process. In some embodiments according to the processes and systems described herein, the bioreactor is connected to a virus filter described herein, where the virus filter is present upstream of the bioreactor.

II. Exemplary Solid Supports

Embodiments disclosed herein provide solid supports modified with a polymer comprising randomly arranged crosslinked monomers. The solid supports encompassed by the present application retain virus contaminants present in a chemically defined cell culture media, even in the presence of cell culture components that are known to rapidly foul virus retention membranes used in downstream virus purification applications. The solid supports encompassed by the present application are resistant to or exhibit reduced fouling by one or more components present in a chemically defined cell culture medium.

Without wishing to be bound by theory, it is contemplated that any suitable solid support format may be used. For example, the solid support can be porous or non-porous or it can be continuous, such as in the form of a monolith or membrane. Exemplary continuous porous solid supports include microporous membranes, i.e. having a pore sizes between about 0.05 micron and 10 micron. Porous membranes that may be used in the compositions and methods according to the embodiments disclosed herein may be classified as symmetric or asymmetric in nature, which refers to the uniformity of the pore sizes across the thickness of the membrane, or, for a hollow fiber, across the microporous wall of the fiber.

As used herein, the term "symmetric membrane" refers to a membrane that has substantially uniform pore size across the membrane cross-section. In a particular embodiment, an asymmetric membrane is used as a solid support. As used herein, the term "asymmetric membrane" refers to a membrane in which the average pore size is not constant across the membrane cross-section. In some embodiments, in case of asymmetric membranes, pore sizes can vary evenly or discontinuously as a function of location throughout the membrane cross-section. In some embodiments, asymmetric membranes can have a ratio of pore sizes on one external surface to pore sizes on the opposite external surface, which ratio is substantially greater than one. An example of an asymmetric membrane which may be modified, as described herein, is a polyethersulfone (PES) membrane. PES membrane can be commercially obtained from vendors such as Sumitomo and Solvay.

A wide variety of membranes made from a wide variety of materials may be used in the compositions and methods described herein. Exemplary polymers that can be used to manufacture the membranes that may be used in the compositions and methods described herein include, but are not limited to, substituted or unsubstituted polyacrylamides, polystyrenes, polymethacrylamides, polyimides, polyacrylates, polycarbonates, polymethacrylates, polyvinyl hydrophilic polymers, polystyrenes, polysulfones, polyethersulfones, copolymers or styrene and divinylbenzene, aromatic polysulfones, polytetrafluoroethylenes (PTFE), perfluorinated thermoplastic polymers, polyolefins, aromatic polyamides, aliphatic polyamides, ultrahigh molecular weight polyethylenes, polyvinylidene difluoride (PVDF), polyetheretherketones (PEEK), polyesters, and combinations thereof.

Exemplary commercially available microporous membranes are Durapore® and Millipore Express® available from EMD Millipore Corp. (Billerica, Mass.); Supor® available from Pall Corp. (Port Washington, N.Y.); and Sartopore® and Sartobran® available from Sartorius Stedim Biotech S.A. (Aubagne Cedex, France). Other exemplary continuous solid supports are monoliths, such as CIM® monolithic materials available from BIA Separations (Villach, Austria).

Examples of commercially available virus retention filters include Viresolve® Pro, Viresolve® NFP and Virosolve® NFR, which function primarily via a size exclusion mechanism. The base membrane substrate used for the manufacture of these virus retention filters may be modified, as described herein, to result in membranes which are resistant to or exhibit reduced fouling by one or more components of a chemically defined cell culture medium.

III. Methods of Modifying Solid Supports

In the compositions and methods described herein, suitable solid supports (e.g., an asymmetric membrane, or specifically, an asymmetric PES membrane) are modified with a polymer comprising randomly arranged and cross-linked monomers of diacetone acrylamide and one or more non-acrylamide cross-linkable monomers (e.g., polyethylene glycol diacrylate).

Various methods are known in the art for modifying the solid supports including the ones described herein.

In various embodiments, the surface of a solid support (e.g., a porous membrane) is modified using an energy source. A variety of energy sources may be used to initiate the modification via a polymerization reaction, e.g., gamma rays, x-rays, free electrons, UV, blue light and heat. Gamma, x-ray, and electron beam methods require no additional chemical initiator to cause polymerization to occur as they are sufficiently energetic to ionize the neutral monomers. However, UV and visible light both require a photoinitiator to generate radical species which then can activate monomers into highly reactive (radicalized) species which in turn can react to form random polymers. This is true for thermally initiated polymerization as well, wherein the initiator may or may not be photo-active, or light activated.

In some embodiments described herein, a solid support (e.g., an asymmetric porous membrane such as a polyethersulfone membrane) is modified using electron beam, as described below.

Typically, using an electron beam process, a membrane is immersed into an appropriate concentration of a mixture of monomers. In case the surface tension of the monomer solution is too high, the membrane sample is pre-wet with a low molecular weight alcohol (like methanol or isopropanol) and is subsequently "exchanged" into a water bath before being immersed into the monomer solution. In some instances, the monomer solution has a sufficiently low surface tension to wet the membrane surface and in this case, the pre-wet and exchange steps are unnecessary. The membrane sample is then withdrawn from the monomer solutions and nip-rolled to remove any excess monomer and to ensure that the monomer solution is evenly distributed on and throughout the entire membrane sample. The membrane sample is then exposed to free electrons by passing the membrane sample under the electron beam under an inerting blanket of nitrogen or argon gas. In some embodiments, a linespeed of 3 to 10 m/minute is used. The electron beam accelerating voltage is set to be between 170 and 200 KV and the beam current in combination with the line speed is adjusted to deliver a 20 to 30 KGy dosage to the membrane sample. These conditions allow the membrane sample to be completely modified through the entire cross-section of the membrane.

IV. Methods of Measuring Throughput Performance of Membranes

In some embodiments, modified solid supports (e.g., a porous membrane) described herein are incorporated into devices, e.g., the devices used in the Examples described herein, and the devices are subsequently used for measuring the throughput performance of the membranes or membrane devices.

The present invention is based, at least in part, on the superior properties of the modified membranes described herein, in that, the throughput performance of the membranes is not adversely affected, even in the presence of membrane fouling components found in chemically defined cell culture media. Accordingly, the methods of modifying solid supports described herein can be used for reducing the fouling of a porous membrane by one or more components of a chemically defined cell culture medium, when filtering the medium through the membrane.

The throughput performance can be measured by first determining the permeability (flux/unit of driving pressure) of the membrane device using a non-plugging feedstream. The non-plugging feedstream is generally comprised of pure water, or an aqueous buffer containing dissolved organic and/or inorganic salts.

The permeability of the membrane or membrane device is defined as the amount of material (in liters or kilograms) per unit area per unit time per unit pressure, often expressed as $L/(m^2\ h\ psi)$, or "liters per meter-squared per hour per psi". If the experiment is run at a constant driving pressure, the device effective filtration area (EFA) and the driving pressure are constants. The only observables are mass of filtrate and time (or volume of filtrate and time). Mass and volume can be used interchangeably when the filtrate density is very close to unity. When the feedstream is not plugging, the permeability remains constant and the "buffer" flux of the device "$J_0$" is determined by the slope of the straight line obtained by plotting mass or volume of filtrate collected vs time.

When the same experiment is run with the plugging stream (e.g., in this case, chemically-defined cell culture media), the flux will decay with time as the device pores become occluded with whatever fouling species the plugging stream contains. This flux is simply referred to as "J". When the relative flux decay, expressed as a percentage (and represented by $(J/J_0)\%$) reaches some pre-determined value, say 25%, the capacity of that device is defined as amount of filtrate (of the plugging feedstream) per unit area of the device that can be recovered by the time the flux has decayed to 25% of the maximum possible flux value of the device, or that flux obtained using the non-plugging feedstream. The capacity as defined in the foregoing description is one numerical or quantitative measure of throughput performance. It is not the only way to measure throughput performance, but it is fairly typical.

Two commonly used points at which device capacities are determined are: (a) when the flux decays to 25% of the maximum device flux (V75—when flux has decayed by 75%); and, (b) when the flux decays to 10% of the maximum device flux (V90—when flux has decayed by 90%). Alternatively, capacity may also be defined as the minimum filtration area needed to filter a fixed amount of a particular feed stream or as a time interval in which to filter a particular amount of a particular feed stream. Any or all of these quantities can be considered as a measure or measures of throughput performance.

V. Methods of Using the Compositions and Devices Described Herein

In various embodiments, the modified virus retentive membranes described herein are used upstream of a bioreactor in order to retain viruses that may be present in a chemically defined cell culture medium prior to transfer into the bioreactor.

For example, in some embodiments, such a virus retentive membrane is incorporated into a device which is then sterilized. The device is then positioned upstream of the bioreactor (at the inlet port) using sterile connectors, and is used to filter a freshly-prepared cell culture medium in a normal filtration mode while the cell culture medium is being transferred into the bioreactor. Consequently, any parvovirus contamination can be reduced to 1/10000 of the level existing before filtration (corresponding to a minimum log reduction value (LRV) of 4).

Embodiments are further illustrated by the following examples which should not be construed as limiting. The contents of all references, patents and published patent applications cited throughout this application, as well as the Figures, are incorporated herein by reference.

EXAMPLES

Example 1: Methods for Modification of a Membrane Surface with a diacetone acrylamide monomer Various methods for modifying a membrane surface with a diacetone acrylamide monomer are explored.

The first method involves dip-coating. A 10% by weight aqueous hexylene glycol solution is prepared. Six grams of diacetone acrylamide (DACm) monomer is dissolved into 194 g of the hexylene glycol-water solution to result in a final solution that is 3% w/w diacetone acrylamide. A 14 cm×14 cm highly asymmetric unmodified hydrophobic polyethersulfone (PES) virus membrane is placed in the DACm solution in a shallow rectangular pyrex baking pan, such that the open face of the membrane comes in contact with the solution first followed by immersion of the membrane into the DACm solution for several minutes. The membrane is withdrawn and placed on an absorbent sheet to remove excess solution and then allowed to air dry on paper towels under ambient air drying conditions. The dry membrane is contacted with Milli-Q water and exhibits instant water wetting. The wet membrane is rinsed with water until no evidence of DACm monomer or hexylene glycol cosolvent residues is found, after which the sample is again air dried. When the re-dried membrane is placed into contact with Milli-Q water, the membrane does not wet. No adsorption of any DACm monomer onto the PES membrane substrate could be demonstrated, as water easily removes the DACm monomer subsequent to the initial monomer treatment.

In another experiment, a 2.00% by weight aqueous DACm solution is prepared by dissolving 4.00 grams of DACm into 196.00 grams of Milli-Q water. The solution is applied by immersion on to a methanol pre-wet (and water exchanged) highly asymmetric, hydrophobic PES virus removal membrane measuring 14 cm×14 cm. The procedure is carried out by contacting the open face of the membrane with the DACm solution in a shallow rectangular pyrex baking pan followed by gentle agitation to immerse the membrane into the solution wherein it is allowed to sit for several (2-3) minutes after which the monomer solution is rinsed off with water until no surfactant activity (bubbles) is observed in the rinse water. After drying and testing for water wetting, it is observed that no DACm remains on the membrane as the membrane remains hydrophobic following the treatment described above. Accordingly, simple adsorption of DACm monomer onto a PES membrane shows no permanent affinity and this dip-coating strategy is not utilized.

In a further experiment, electron beam polymerization of DACm onto a membrane is investigated. In this experiment, the same 2.00 weight % aqueous solution of DACm monomer is applied to another identical highly asymmetric hydrophobic PES virus removal pre-wet membrane after which the membrane is nipped between two 100 um thick clear polypropylene sheets to remove excess monomer solution. The membrane is then passed under an electron-beam source (for a 25 KGy exposure to 170 KeV electrons) to polymerize the DACm monomer onto the membrane. Surprisingly, the resulting membrane is slow to wet in water even though the monomer itself is readily water soluble. However, the resultant membrane wet completely in a Milli-Q water bath within 45 seconds, indicating that a DACm homopolymer is formed on the membrane by this treatment. The treated membrane is also observed to be impervious to autoclave and dry heat, even though no cross-linking monomer is used in combination with the DACm monomer. Further, no change in water wetting behavior or water permeability is observed after a 2 hour room temperature soak in 0.2M NaOH(aq). However, the coating does wash off with methanol.

Further testing in 0.5M NaOH over a 16 hour static soak demonstrates that the resulting homopolymer membrane is caustic stable up to 4 hours, after which, the homopolymer surface modification begins to deteriorate. This is demonstrated by modifying a series of identical preweighed membrane samples, using the same monomer solution and subjecting them to the identical e-beam initiated polymerization process. The samples are again weighed after surface modification and drying and any add-on weight by diacetone acrylamide homopolymer is determined for each membrane sample. These membrane samples are then immersed in a 0.5M NaOH solution and withdrawn one at a time at successive time intervals. It is observed that the surface modification starts to deteriorate only after 4 hours.

Although the electron beam initiated polymerization of DACm onto a membrane is successful compared to the other methods described above, the effect on membrane throughput needs to be investigated.

Example 2: Throughput Performance of DACm Homopolymer-Modified Membranes Using Electron Beam Initiated Polymerization with and without Pluronic F68 Exposure A range of aqueous DACm solutions are prepared at 2, 4, 6, 8, and 10 weight %. These solutions are then used to surface modify highly asymmetric hydrophobic PES membrane measuring 14 cm×14 cm using the electron beam process described above.

The membranes are then subject to throughput testing as per the following outlined procedure.

Circular membrane samples, 25 mm in diameter, are cut from each of the modified membranes prepared as described above and assembled into over-molded microscale filter devices. The devices include a housing with a fluid inlet on top and a fluid outlet at the bottom with the disk-shaped filter element contained in the central radial portion of the housing. Each fluid inlet has an integral vent to allow air and fluid to escape and purge the volume directly above the actual filter element.

Each device is connected to two fluid delivery manifolds, constructed of 0.25 inch polypropylene tubing by a sub-manifold assembled from a 0.25 inch polypropylene tubing as well as compatible Luer fittings and valves. One manifold delivers Milli-Q water (non-plugging stream) to each of the devices and the other manifold delivers chemically defined cell culture media dissolved in Milli-Q water (plugging stream) to each of the devices. Each manifold is constructed to support and supply 10 such filter devices. Each of the fluid delivery manifolds is connected to a separate pressure vessel, which acts as a test fluid reservoir. Each pressure vessel is supplied individually by a regulated pressurized air supply set to deliver fluid to the devices at 30 psi or approximately 2 bar ($2\times10^5$ Pa). A load cell with a fluid collection container is mounted below each filter device to measure the mass of the collected filtrate as a function of time. Each load cell is connected to a multi-channel data acquisition board which is in-turn interfaced to a computer running data acquisition software to record the filtrate mass collected (in grams) versus time (in adjustable units, but typically in minutes).

Additionally, the effect of Pluronic F68 membrane exposure or pre-treatment is investigated. Pre-treatment or exposure to Pluronic F68 involves passing several (~5) milliliters of a stock aqueous 10% (100 g/Liter) Pluronic F68 solution through each filter assembly by syringe followed by a copious extractive rinse with Milli-Q water until no froth or bubbles are observed in the rinse water while the Milli-Q water rinse is being carried out.

It is observed that the samples pre-treated with Pluronic F68 show improved throughput performance over those samples without the Pluronic F68 pre-treatment. These results indicate that DACm treated membranes may offer enhanced fouling resistance to cell culture media containing Pluronic F68. The throughput performance test results are summarized below in Table I and also shown in FIG. 1.

Throughput performance is quantitatively referred to as the membrane capacity. Accordingly, the membrane capacity is feed stream dependent. Capacities are represented in this experiment by two measurements, referred to as V75 and V90, which correspond to Liters of filtrate collected per square meter of effective membrane surface area when flux has decayed to 25% and 10%, respectively, of the initial flux (in units of [$L/m^2$]). Initial flux is determined from membrane permeability, which is in turn determined by measuring the volume of non-plugging stream passed through a membrane per unit time per driving pressure. Membrane permeability herein is represented in units of Liters of filtrate collected per unit area ($m^2$) per unit time (hrs) per unit driving pressure (psi), or [$L/(m^2$ h psi). The driving pressure of 30 psi is used for this and subsequent throughput experiments.

Table I depicts the membrane throughput performance results for diacetone acrylamide homopolymer modified membranes without (rows 1-5) and with ($2^{nd}$ 5 rows 6-10) Pluronic F68 exposure or pre-treatment.

TABLE I

| Device with modified membrane | V75 | V90 | 10XPerm | Vol@150 min | Final Volume (ml) | Final Time (min) |
|---|---|---|---|---|---|---|
| 2% DACm | 160 | 392 | 341 | 133 | 133 | 147 |
| 4% DACm | 87 | 300 | 416 | 125 | 125 | 147 |
| 6% DACm | 132 | 430 | 351 | 125 | 134 | 147 |
| 8% DACm | 138 | 420 | 293 | 125 | 126 | 151 |
| 10% DACm | 210 | 500 | 331 | 155 | 154 | 148 |
| 2% DACm F68 | 280 | 550 | 294 | 155 | 170 | 180 |
| 4% DACm F68 | 140 | 415 | 265 | 118 | 118 | 148 |
| 6% DACm F68 | 207 | 540 | 315 | 149 | 163 | 177 |
| 8% DACm F68 | 235 | 540 | 287 | 145 | 164 | 187 |
| 10% DACm F68 | 290 | 600 | 294 | 162 | 178 | 177 |

In general, it is observed that the throughput performance of the membranes increases with increasing DACm levels used for membrane treatment, all the way up to 10%. Additionally, an improvement in throughput performance is observed for the DACm modified membranes that are pre-treated with or exposed to Pluronic F68 relative to the membranes not pre-treated with or exposed to Pluronic F68. Therefore, Pluronic F68 does not appear to have a fouling effect on the DACm modified membranes.

However, leaching tests with the foregoing membranes showed that, at least for the higher DACm levels, DACm homopolymer leached upon contact with methanol, after which the membrane flow characteristics and wettability were impacted. The leaching tests suggest that without cross-linking the DACm monomer, it is not possible to assure low extractables and achieve consistent membrane performance. Furthermore, accidental exposure to low molecular weight alcohols presents an undesirable material vulnerability.

Example 3: Selection of Crosslinkers for the DACm Monomer

Several potential crosslinkers for the DACm monomer are tested in this Example. Tetraethylene glycol diacrylate (TEDGA) is investigated as a potential crosslinker for the DACm monomer. However, the modification with DACm and TEGDA does not produce a stable cross-linked surface modification. Subsequently, a water-soluble and non-acrylamide crosslinking monomer, polyethylene glycol diacrylate (PEGDA), is tried as the crosslinker in place of TEGDA. A 575 average MWt PEG diacrylate (PEGDA575) is reported as possessing the best water solubility of the available MWt PEG diacrylates. The first crosslinker level that is tested is 1%.

To select a starting DACm level for combination with the crosslinker, the 2 to 10 Wt % DACm homopolymer modified membranes are again inspected for water-wetting speed and permeability. It is found that the 4% DACm-modified membrane wets out faster and more uniformly in water than the other DACm homopolymer modified membranes. Consequently, 4.00% DACm is selected as the starting DACm level to be used in a crosslinked surface modification chemistry with 1% PEGDA575. The monomer mix is applied by e-beam in the same fashion as that described above, with the exception that the monomer solution is comprised of 4.00 Wt % DACm monomer in combination with 1.00 Wt % PEGDA monomer in 95 Wt % of Milli-Q water.

The effectiveness of the crosslinking, characterized by the permanence of this coating, is confirmed by soaking the resulting modified membrane samples in methanol followed by water rinse and drying, and then retesting the wetting and permeability. The results of water wetting and water permeability tests are essentially identical to those recorded before the methanol extraction step. Therefore, the modification is considered to be stable.

Further, in a separate experiment, the use of a non-acrylamide crosslinker is investigated and compared to an acrylamide crosslinker, with respect to the effect on membrane throughput performance. PEGDA575 is used as the non-acrylamide cross-linkable monomer and methylene-bis-acrylamide (MBAm) is used as an acrylamide cross-linkable monomer. An experimental prototype chemically defined CHO cell culture medium, MX-201 or Beta-CHO, is used as the plugging or fouling feed stream in this experiment. Each cross-linking monomer (PEGDA or MBAm) is used at an identical 1.00 weight percent treat level (1.00 Wt %). Each of these cross-linkers is separately combined with 4% DACm (diacetone acrylamide) to form the polymer mix using Milli-Q water as solvent.

Figure 2:
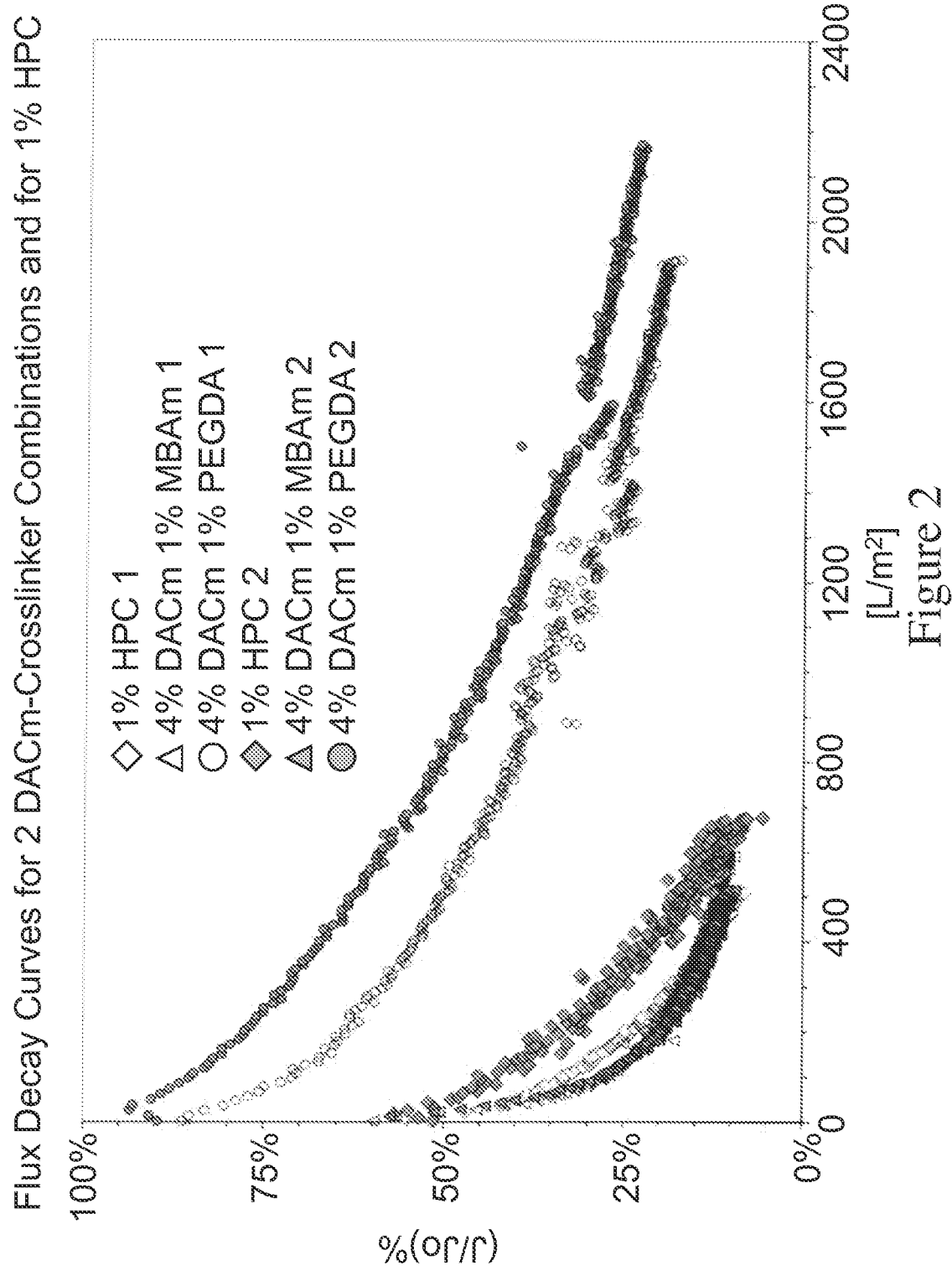
FIG. 2 depicts flux decay curves for membrane devices containing 4% DACm-1% MBAm modified PES membrane or 4% DACm-1% PEGDA modified PES membrane or a 1% HPC modified PES membrane (as control), tested in duplicate. The Y-axis represents the flux decay represented as a percentage of (J/J$_0$) %, which is the percentage based on the flux J$_0$ determined for a non-plugging or non-fouling feedstream (e.g., Milli-Q water) and the X-axis represents the throughput or capacity of membranes expressed by liters of filtrate collected per square meters of membrane (L/m$^2$).

FIG. 2 represents flux decay curves for duplicate 25 mm diameter membrane devices, each with one of three surface modified membranes. These are: (a) 4% DACm-1% MBAm; (b) 4% DACm-1% PEGDA575; and (c) 1% HPC.

Figure 3:
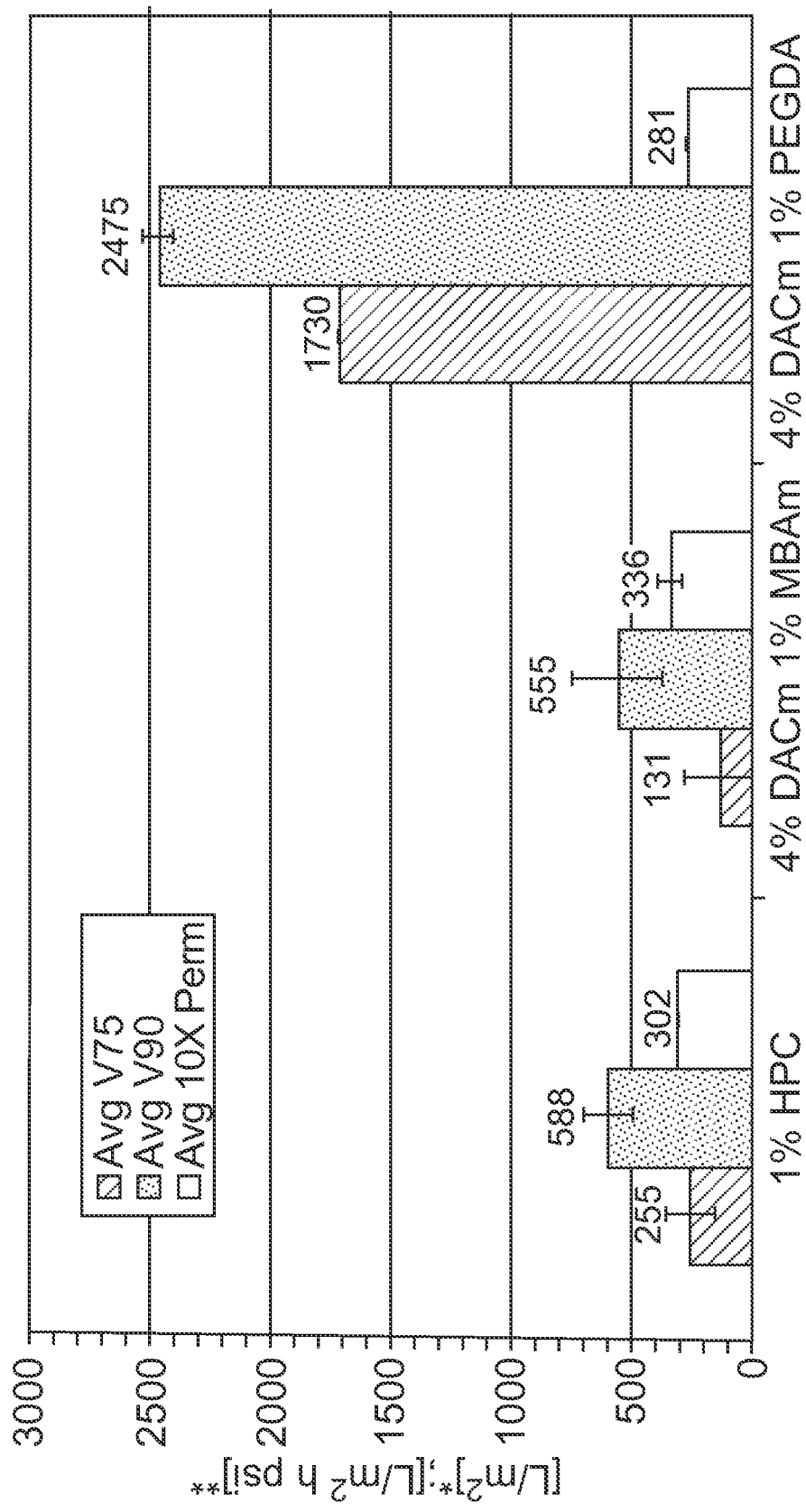
FIG. 3 depicts a bar graph depicting the capacities and permeabilities of 4% DACm-1% MBAm, 4% DACm-1% PEGDA and 1% HPC (as control) surface modified PES membranes. A CHO cell chemically defined cell culture medium is used as the feedstream. The X-axis represents the membrane and the Y-axis represents V75 (L/m$^2$), V90 (L/m$^2$) and 10× permeability (L/m$^2$ h psi).

Table II below summarizes the results of one such experiment used to measure flux decay, V70, V90 and 10× permeabilities, also as depicted in FIG. 3, which depicts capacities and permeabilities of 4% DACm-1% MBAm and 4% DACm-1% PEGDA modified PES membranes relative to the 1% HPC control membrane. A chemically defined CHO cell culture medium is used as the feedstream.

As observed, 4% DACm-1% MBAm membrane exhibits lower throughput performance relative to 1% HPC membrane. However, the 4% DACm-1% PEGDA575 membrane exhibits higher throughput performance relative to 1% HPC.

TABLE II

| Membrane ID | Avg V75 | Avg V90 | Avg 10X Perm | SD V75 | SD V90 | SD 10X Perm |
|---|---|---|---|---|---|---|
| 1% HPC | 255 | 588 | 302 | 99.7 | 109.6 | 3.54 |
| 4% DACm 1% MBAm | 131 | 555 | 336 | 7.1 | 63.6 | 4.24 |
| 4% DACm 1% PEGD A | 1730 | 2475 | 281 | 325.3 | 176.8 | 4.95 |

*SD stands for standard deviation

Accordingly, a non-acrylamide based cross-linkable monomer (e.g., PEGDA) is a far better choice to use with DACm compared to an acrylamide based cross-linkable monomer (e.g., MBAm).

Example 4: Comparative Throughput Performance Testing of Crosslinked Copolymer Modified Membranes The surface modifications are further tested in a manner identical to the methodology described previously for throughput performance. The following results are taken from the first capacity tests carried out with DACm-PEGDA575 copolymer chemistry.

As explained in the previous example with DACm homopolymer, all the quantities presented below in Table III have the same meaning and units, except that the average values for duplicate samples are presented.

Table III depicts the average capacities (V75 and V90 in units of [L/m$^2$] and permeabilities in units of [L/(m$^2$ h psi]) for duplicate capacity determinations from the first comparative test using DACm-PEGDA575 copolymer membrane surface modification chemistry.

TABLE III

| Surface Modification | Average V75 [L/m$^2$] | Average V90 [L/m$^2$] | Average Permeability [L/(m$^2$ h psi)] |
|---|---|---|---|
| 1L-1% HPC | 255 | 588 | 30.2 |
| 1L-3.75% LB20 | 532 | 893 | 35.6 |
| 1L-4.00% DACm-1.00% MBAm | 131 | 555 | 33.6 |
| 1L-2.00% LB20-1.00% HEA-0.75TEGDA | 675 | 995 | 27.2 |
| 1L-4.00% DACm-1.00% PEGDA575 | 1730 | 2475 | 28.1 |

All devices are constructed with the same starting membrane material (highly asymmetric unmodified hydrophobic PES virus retentive membrane with a 20 nm nominal pore size rating). Each filter device is constructed to house a single layer (1L-) of each of the various surface modified membranes. The surface modification chemistries applied onto each membrane sample are described below.

HPC is an adsorbed polymer pretreatment applied by immersion and comprising an aqueous 1.00 Wt % hydroxypropyl cellulose solution with 10% hexylene glycol used as a membrane wetting aid. LB20 is a self-crosslinking highly-ethoxylated triacrylate monomer applied by in situ electron beam curing. DACm stands for diacetone acrylamide, a monofunctional vinylic monomer, and MBAm stands for methylene-bis-acrylamide, a diacrylamide crosslinker which forms a copolymer with DACm. HEA stands for hydroxyethyl acrylate, a monofunctional vinylic monomer. TEGDA stands for tetraethylene glycol diacrylate, a difunctional or crosslinking monomer, as is PEGDA575, which is a 575 number-average MWt polyethylene glycol diacrylate. DACm-MBAm is a copolymeric surface modification applied by electron beam curing as is DACm-PEGDA575. LB20, HEA, and TEGDA form a terpolymeric surface modification, also applied onto the membrane by an electron beam curing process.

Figure 4:
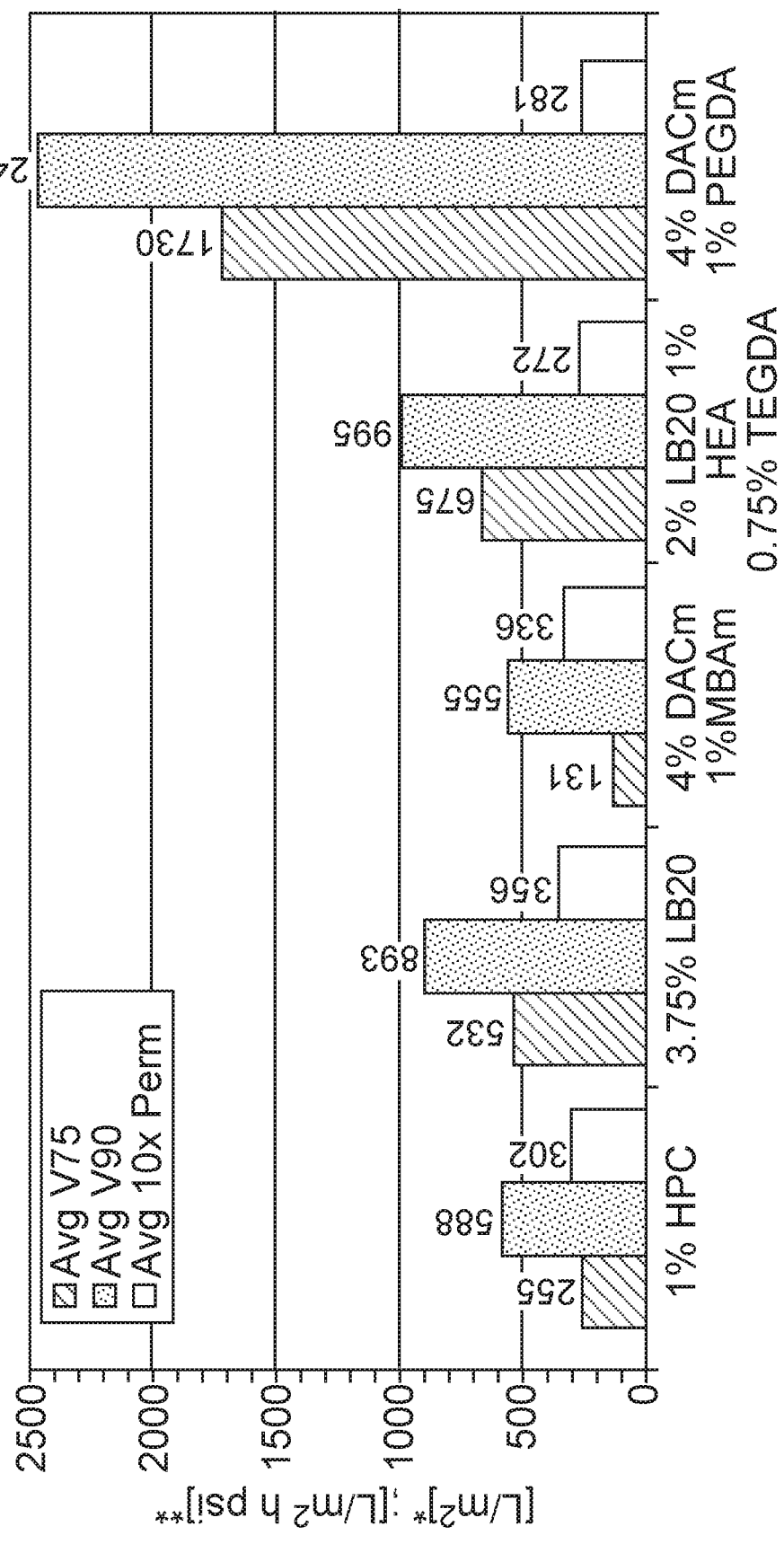
FIG. 4 is a bar graph depicting the average capacities and permeabilities of the various membrane devices tested, as measured V75, V90 and 10× permeability. Each membrane device is constructed to house a single layer (1L-) of each of the various surface modified membranes. 1% HPC refers to a single layer membrane device having an adsorbed polymer pretreatment applied by immersion and comprising an aqueous 1.00 Wt % hydroxypropyl cellulose (HPC) solution with 10% hexylene glycol used as a membrane wetting aid; 3.75% LB20 refers to a single layer membrane device having a self-crosslinking highly-ethoxylated triacrylate monomer applied at concentration of 3.75% by in situ electron beam curing; 4.00%-DACm-1% MBAm refers to a single layer membrane device having 4% diacetone acrylamide (DACm), a monofunctional vinylic monomer, and 1% methylene-bis-acrylamide (MBAm), a diacrylamide crosslinker which forms a copolymer with DACm; 2.00% LB20-1% HEA-0.75% TEGDA refers to a single layer membrane device having 2% LB20, 1% hydroxyethyl acrylate (HEA), and 0.75%, a tetraethylene glycol diacrylate, a difunctional or crosslinking monomer; and 4.00%-DACm1%-PEGDA575 refers to a single membrane device having 4% DACm and 1% PEGDA575, which is a 575 number-average MWt polyethylene glycol diacrylate.

FIG. 4 is a bar graph depicting the average capacities and permeabilities of the various membrane devices tested, as described above. As seen in FIG. 4, a significant improvement in throughput performance is observed for the DACm-PEGDA575 copolymer modified membrane device relative to the other modifications tested in this Example.

Figure 5:
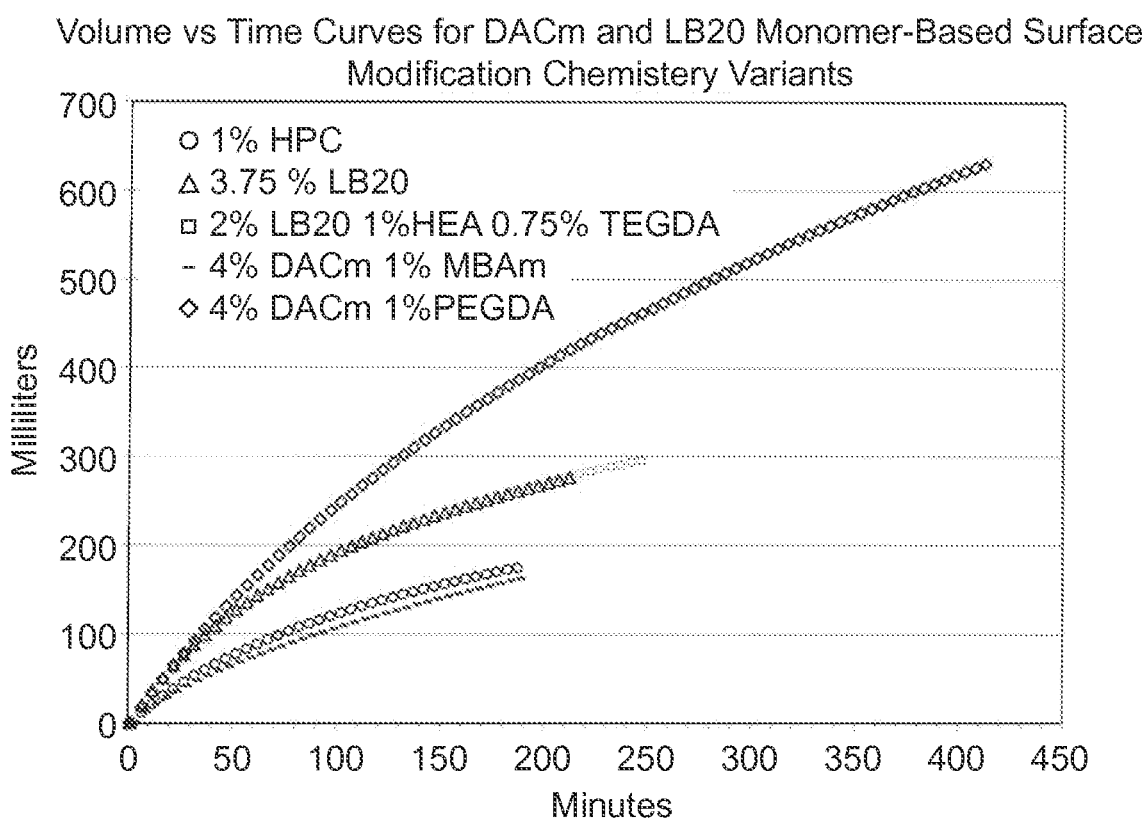
FIG. 5 depicts a graph representing average volume versus time curves for each of the single layered membrane devices tested in duplicate. The membrane devices tested are: 1% HPC; 3.75% LB20; 4.00% DACm-1% MBAm; 2.00% LB20-1% HEA-0.75% TEGDA; and 4.00%-DACm1%-PEGDA575. The X-axis represents volume (mls) of filtrate collected after passing a CHO cell culture media through the various membrane devices; and the Y-axis represents time (mins).

FIG. 5 depicts volume versus time curves for each of the devices tested herein. As depicted in FIG. 5, a much higher quantity of filtrate was collected for the DACm-PEGDA575 copolymer modified membrane device relative to the other modifications tested in this Example.

In a further experiment, a chemically defined CHO cell culture medium, MX-201 (or Beta-CHO), is used as the feed stream. V-Pro membrane (PHHC membrane modified with 1% hydroxypropyl cellulose) containing devices are used as controls. Devices labeled as 375LB20 are made with a 3.75% LB20 (20 mole-ethoxylated trimethylol propane triacrylate) monomer mix made up in Milli-Q and cured onto the membrane by e-beam. Devices labeled as 200L, 100H and 075T are 2% LB20, 1% HEA, and 0.75% TEGDA, respectively, all dissolved in Milli-Q water. The devices labeled as 4DACm1PEGDA include 4% DACm and 1% PEGDA575 in Milli-Q water. All chemistries are applied with a 25 KGy e-beam dosage.

A very significant increase in throughput performance of the 4DACm1PEGDA device is observed relative to the other candidate chemistries tested.

In a further experiment, PEGDA575 on identical membrane devices as described above, is tested on its own at concentrations ranging from 2% to 5% (also prepared by the same e-beam process as described above) and throuput performance is comparable to that obserbed with the 4DACm1PEGDA device.

Subsequently, the same chemically defined cell culture media as described above is used with a device containing 5% PEGDA575. An improved throughput performance advantage is again confirmed.

In a yet further experiment, compositions containing DACm and PEGDA monomers at different concentrations are evaluated for throughput performance of membranes modified with the these monomers. The following compositions are prepared and tested: compositions containing 4% DACm with 0.75%, 1.25%, 1.50% 2.00% and 2.50% PEGDA are prepared. In addition, a composition containing 3% DACm with 3% PEGDA575 is prepared.

Figure 6:
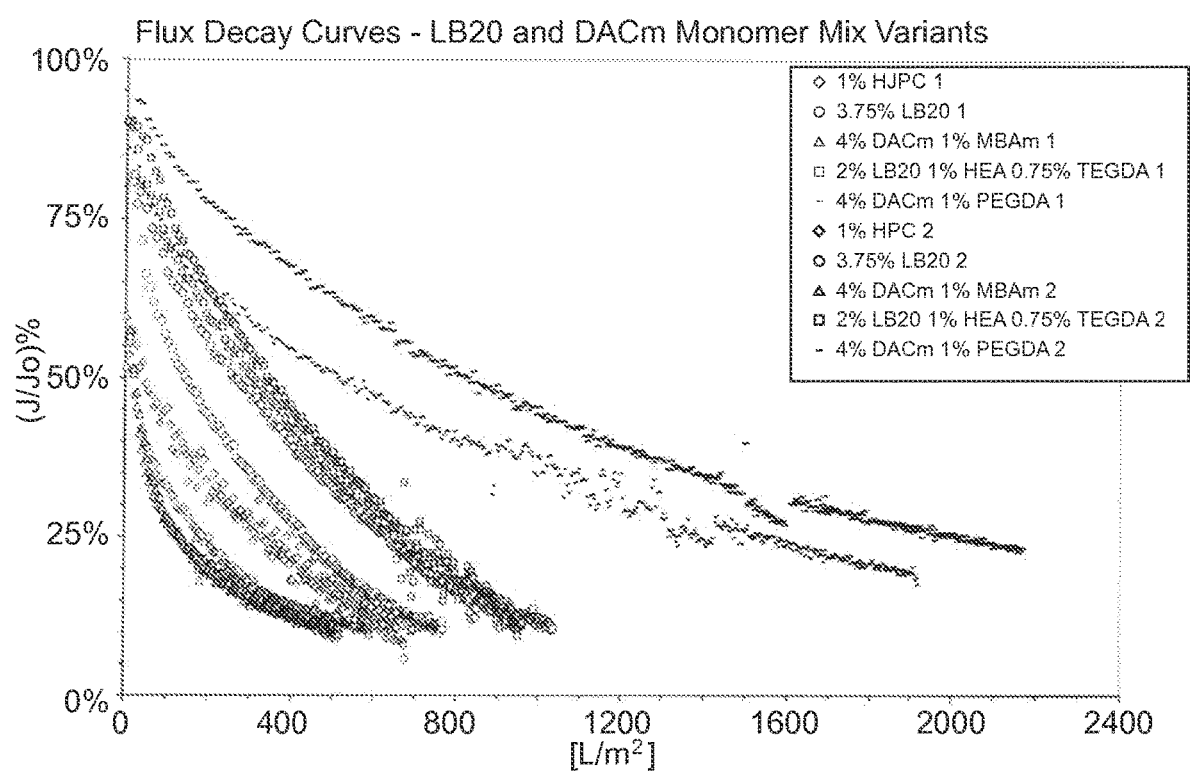
FIG. 6 depicts a graph representing flux decay curves obtained from each of the single layered membrane devices tested in duplicate. The membrane devices tested are: 1% HPC; 3.75% LB20; 4.00% DACm-1% MBAm; 2.00% LB20-1% HEA-0.75% TEGDA; and 4.00%-DACm1%-PEGDA575. The X-axis represents membrane capacity (L/m$^2$) and Y-axis represents flux decay (J/J$_0$). As depicted in FIG. 6, the DACm-PEGDA575 copolymer modified membrane device had a throughput performance advantage over the other modifications tested, by way of a slower flux decay.

FIG. 6 depicts flux decay curves obtained from each of the membrane devices tested. As depicted in FIG. 6, the DACm-PEGDA575 copolymer modified membrane device has a throughput performance advantage over the other modifications tested, by way of a slower flux decay.

Example 5: Evaluation of Thermal Stability of DACm-PEGDA Copolymer Modified Membranes DACm-PEGDA copolymer modified membranes are further evaluated for thermal stability, as thermal stability is desirable for sterilization.

Thermal stability is addressed by subjecting modified membrane to wet autoclave conditions (1 Hr cycle at 134° C.), dry heat conditions (1 Hr cycle at 135° C.), and steam-in-place (SIP) conditions (½ Hr live steam-in-place cycle).

Autoclave treatment involves subjecting an object (membrane or device, in this case) to a static closed chamber heating cycle with water under conditions in which liquid water exists in equilibrium with its vapor above atmospheric pressure for a time interval over and above that necessary to sterilize the object.

Dry heat treatment involves, just as the term suggests, subjecting an object (membrane or device) to dry air at some predetermined temperature (in this case) equivalent to the autoclave temperature described in a convection oven to determine whether conditions that might be encountered during device fabrication might compromise the object's performance.

Steam-in-place treatment involves subjecting an object (membrane or device) to live steam under dynamic conditions in which the steam is non-condensing (at a specific temperature and pressure above the boiling point of water) and is transported through the membrane or the device housing the membrane or some like (filter) element so as to sterilize all surfaces exposed to the steam.

In each case, the membrane capacities are tested by fabricating micro-scale devices, as described above, with the thermally treated membranes, measuring throughput performance, and comparing throughput performance results with those obtained from non-heat-treated devices as controls.

In the first set of experiments, the membranes are exposed to wet autoclave conditions.

All devices except the 1L-1% HPC control are fabricated with monomer mixes containing 4.00% diacetone acrylamide (DACm). The PEGDA575 level is varied and Includes 1.00% 1.25% and 1.50%. Some devices use a 2-layer filter element and are designated as 2L-.

Table IV depicts membrane throughput performance, as measured by V75, V90 and 10× permeabilities of the various membranes, either following no-thermal treatment, or following autoclaving of the devices or following autoclaving of the membranes before device fabrication.

TABLE IV

| Device ID | V75 [L/m²] | V90 [L/m²] | 10X Perm [L/m² h psi] |
|---|---|---|---|
| 1L-4% DACm-1% PEGDA575 AM | 475 | 1100 | 303 |
| 2L-4% DACm-1% PEGDA575 AM 1 | 1300 | 1700 | 154 |
| 1L-4% DACm-1% PEGDA575 ACD | 675 | 1500 | 313 |
| 1L-4% DACm-1.25% PEGDA575 ACD | 500 | 1400 | 266 |
| 1L-4% DACm-1.5% PEGDA575 ACD | 1500 | 2500 | 273 |
| 2L-4% DACm-1% PEGDA575 AM 2 | 2100 | 3000 | 199 |
| 1L-4% DACm-1% PEGDA575 ACM | 885 | 1500 | 301 |
| 1L-4% DACm-1.25% PEGDA575 ACM | 1250 | 1800 | 300 |
| 1L-4% DACm-1.5% PEGDA575 ACM | 1700 | 2500 | 280 |
| 1L-1% HPC | 185 | 460 | 329 |

AM = As Modified (no thermal treatment);
ACD = Autoclaved Devices; and,
ACM = Autoclaved Membrane (followed by device fabrication before testing)

Figure 7:
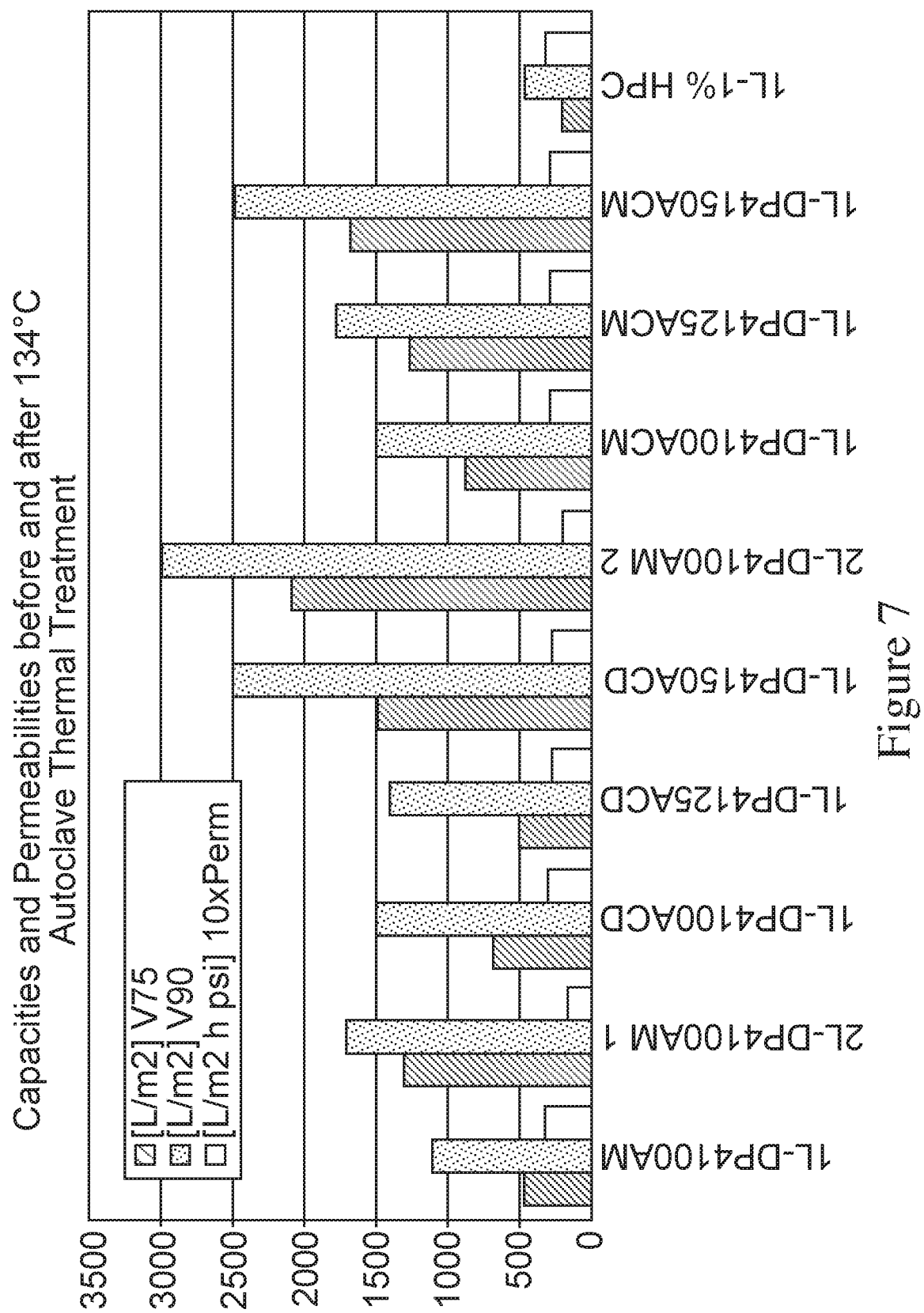
FIG. 7 depicts a bar graph representing capabilities and permeabilities of a series of various membrane devices before and after thermal treatment, as measured by V75 (L/m$^2$), V90 (L/m$^2$) and 10× permeability (L/m$^2$ h psi). The membrane devices tested are in three categories: modified membrane with no thermal treatment (AM), which are as follows-1L-DP4100 AM (i.e., 4.00%-DACm1%-PEGDA); 2L-DP4100 AM1; and 1L-DP4100 AM2; modified membrane autoclaved in device at 134° C. for 1 hour (ACD), which are as follows-L-DP4100 ACD; 1L-DP4125 ACD (i.e., 4.00%-DACm1.25%-PEGDA) and 1L-DP4 150 ACD (i.e., 4.00%-DACm1.50%-PEGDA); modified membrane autoclaved at 134° C. for 1 hour rollowed by device configuration (ACM), which are as follows-1L-DP4100 ACM; 1L-DP4125 ACM and 1L-DP4150 ACM. A single layer 1L-1% HPC membrane is used as a control. The X-axis represents the various membrane devices and the Y axis represents the capacities V75, V90 and 10× permeabilities, as determined using 4 g/L human plasma-derived IgG in acetate buffer at pH 4 and 2 mS/cm conductivity.

The results of one such representative experiment are depicted in FIG. 7, which depicts the membrane throughput performance of the various membranes, as measured using V75, V90 and 10× permeabilities, either following no thermal treatment (AM), following autoclaving of the membrane containing devices (ACD) or following autoclaving of the membranes prior to device fabrication (ACM). The performance results Include membrane device permeabilities (constant flow of non-plugging stream (water) with micro-scale devices (3.1 cm² effective filtration area (EFA)), and capacities determined at V75 and V90, determined using 4 g/L human plasma-derived IgG in acetate buffer at pH 4 and 2 mS/cm conductivity. In FIG. 7, 1L and 2L stand for one layer and two layer membrane devices, respectively; DP4100 stands for 4.00% DACm and 1.00% PEGDA; DP4125 stands for 4.00% DACm and 1.25% PEGDA; and DP4150 stands for 4.00% DACm and 1.50% PEGDA.

As observed, for most part, for all membrane devices which are subjected to autoclaving, either device containing the membrane is autoclaved or membrane is autoclaved prior to device fabrication, the membrane performance appears to improve with an increase in the PEGDA level, as well as over the control 1L-1% HPC membrane.

In another experiment, a similar but not completely identical series of membrane devices are exposed to dry heat cycle (135° C. for 1 Hr). In this experiment, all membranes are fabricated into single layer devices. Experimental membrane devices are fabricated with membranes modified using a monomer mix that contains 4.00% diacetone acrylamide (DACm) and 1% PEGDA575 (DP4100), or with a monomer mix that contains 4% DACm and 2% PEGDA575 (DP4200). Controls devices (2) are made by modifying starting membranes with an adsorbed coating of 1% hydroxypropylcellulose (1% HPC) which are fabricated into identical devices as the devices housing the membranes modified with the DACm and PEGDA. The membrane which is modified is a PES membrane from two separate sources, referred to as P1 and P2.

Figure 8:
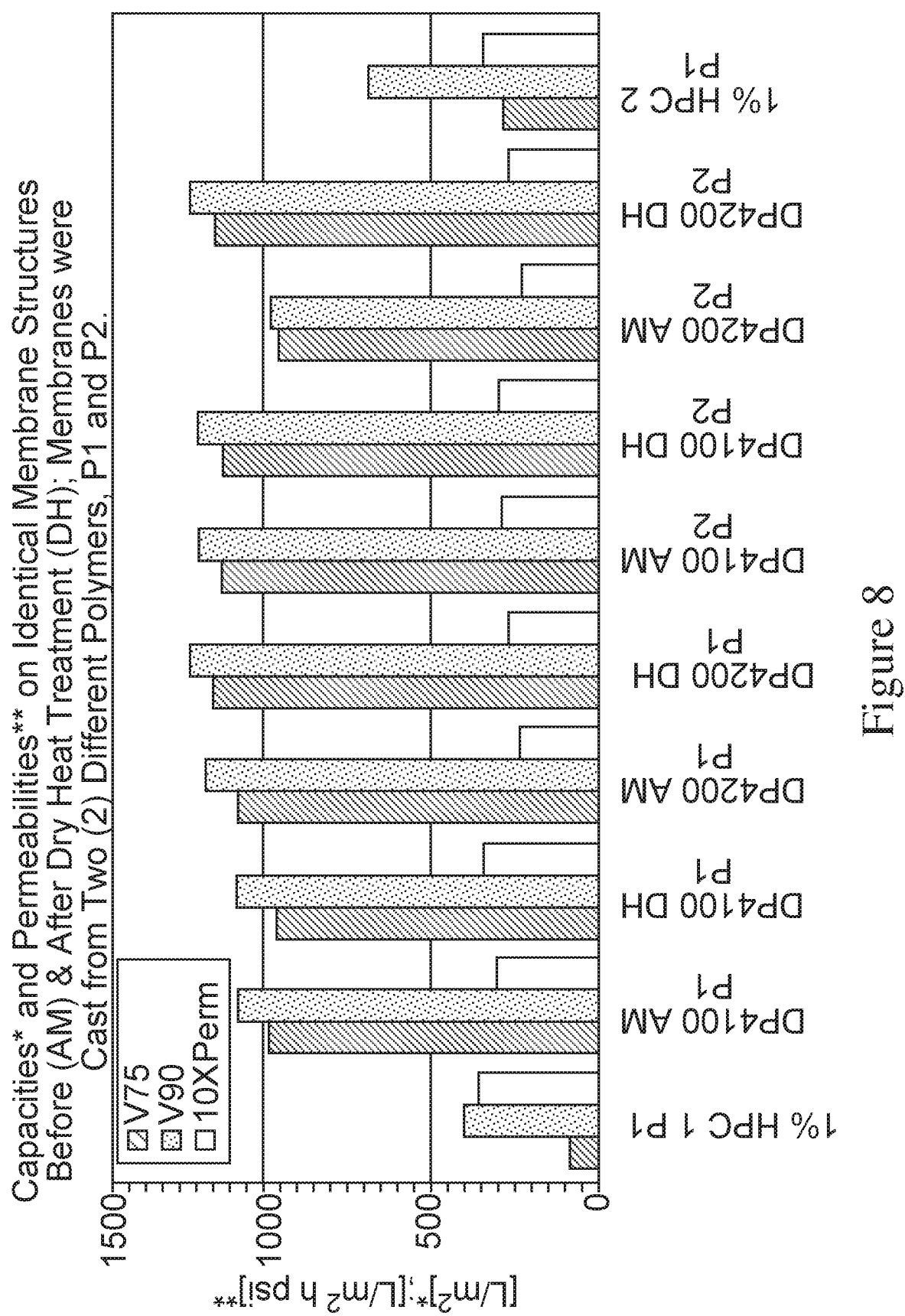
FIG. 8 is a bar graph representing capacities and permeabilities of membranes before (AM) and after dry heat treatment (DH), as measured by V75 (L/m$^2$), V90 (L/m$^2$) and 10× permeability (L/m$^2$ h psi). Membranes tested were cast from PES polymers from two different sources, referred to as P1 and P2 herein. The membrane devices tested are: 1% HPC P1 and 1% HPC P2 as controls; modified membranes with no thermal treatment (AM), which are as follows-DP4100 AM P1; DP4200 AM P1 (i.e., 4.00%-DACm2.00%-PEGDA); DP4100 AM P2 and DP4200 AM P2; modified membranes treated with dry hear (DH), which are as follows-DP4100 DH P1, DP4100 DH P2 and DP4200 DH P2. The X-axis represents the various membrane devices and the Y axis represents the capacities V75, V90 and 10× permeabilities, as determined using 4 g/L human plasma-derived IgG in acetate buffer at pH 4 and 2 mS/cm conductivity.

Table V presents the results of one such experiment, as also depicted in FIG. 8. The membrane throughput performance is measured using V75, V90 and 10λ permeability values, as previously described. As observed, the capacities (V75 and V90) of all experimental devices containing modified membranes are very similar, regardless of the differences between membrane modification formulations (DP4100, DP4200), and regardless of whether or not the membranes are subjected to the dry heat thermal treatment; however, the capacities of the modified membranes in general are higher than that of the control membranes (1L-1% HPC P1 and 1L-1% HPC P2). Interestingly, however, the performance improvement obtained with increased PEGDA level, as seen with autoclave treatment is not observed using dry heat treatment.

Table V depicts the capacity and permeability results from a comparative throughput experiment using devices fabricated with as-modified membrane samples (AM) and comparing to identical devices subjected to an additional dry heat thermal treatment (135° C., 1 hour).

TABLE V

| Device ID | V75 [L/m²] | V90 [L/m²] | 10X Perm [L/m² h psi] |
|---|---|---|---|
| 1% HPC P1 | 65 | 393 | 348 |
| DP4100 AM P1 | 1000 | 1100 | 288 |
| DP4100 DH P1 | 975 | 1100 | 333 |
| DP4200 AM P1 | 1100 | 1200 | 225 |
| DP4200 DH P1 | 1175 | 1250 | 261 |
| DP4100 AM P2 | 1150 | 1225 | 280 |
| DP4100 DH P2 | 1150 | 1225 | 291 |
| DP4200 AM P2 | 975 | 1000 | 219 |
| DP4200 DH P22 | 1175 | 1250 | 261 |
| 1% HPC P2 | 275 | 700 | 339 |

AM = As Modified Devices (no thermal treatment);
DH = Dry Heat Cycled Devices.
P1 and P2 represent PES membranes from two different sources.
1% HPC identifies control membrane devices (used in duplicate).

In yet another experiment, the various membrane devices are subjected to a steam-in-place (SIP) process to determine how the standard steam-in-place process impacts throughput performance (water permeability, media capacity, retention).

The chemistries described herein are applied to membranes from two different PES membrane sources (membranes P1 and P2). One half of the prepared membrane samples are subject to SIP conditions. All membrane samples are assembled into microscale devices and are both are tested for throughput performance (permeability and capacity), and also for retention of virus-like particles.

Table VI presents results of an experiment in which permeability, feed throughput, capacity, and the retention of a bacteriophage are determined for various membranes. The feed consists of experimental MX-201 (Beta-CHO) cell culture media in Milli-Q water spiked with 1×10⁸ pfu/uL PHI-X174 bacteriophage. The results are determined for single membrane element 25 mm diameter micro-scale devices (3.1 cm² EFA). Each device contains a different membrane either with the as-modified (AM) designation which are not subjected to any thermal treatment, or with the stream-in-place (SIP) designation. All membranes are PES in composition and manufactured from one of two different polymer sources referred to and identified as either P1 or P2. Each membrane is run in duplicate with duplicates identified as either A or B. Membranes identified as 1% HPC are not subject to SIP treatment for this test. These are used as controls and serve to demonstrate a level of variability in device performance. These membrane devices are fabricated from the P1 polymer modified with 1% HPC. Membranes identified as DP4100 are modified using the 4% DACm—1% PEGDA inventive surface modification embodiment which is applied to both the P1 polymer and the P2 polymer membranes.

TABLE VI

| Membrane ID | Permeability (LMH/psi) | V120 min (mL) | Amin (m²) | Initial LRV | Final LRV |
|---|---|---|---|---|---|
| 1% HPC P1 A AM | 25.57 | 419.20 | 1.69 | 4.8 | 4.9 |
| 1% HPC P1 B AM | 27.44 | 426.12 | 1.73 | 5.6 | 5.6 |
| DP4100 P1 A AM | 22.78 | 641.74 | 1.13 | 5.6 | 5.4 |
| DP4100 P1 A SIP | 22.95 | 597.19 | 1.17 | 5.9 | 5.7 |
| DP4100 P2 A AM | 23.48 | 684.50 | 1.02 | 5.3 | 5.0 |
| DP4100 P2 A SIP | 24.25 | 679.53 | 1.03 | 5.3 | 5.4 |
| DP4100 P1 B AM | 24.69 | 674.16 | 1.07 | 5.5 | 5.2 |
| DP4100 P1 B SIP | 24.41 | 685.41 | 1.09 | 5.2 | 4.9 |
| DP4100 P2 B AM | 22.80 | 659.67 | 1.04 | 5.5 | 5.5 |
| DP4100 P2 B SIP | 23.39 | 667.69 | 1.08 | 5.2 | 4.9 |

Permeability is determined by passing non-plugging buffer (Milli-Q water in this case) through the device for a 10 to 15 minute interval and recording the quantity of buffer collected. The plugging stream containing the cell culture media dissolved in Milli-Q water is then passed through the device. Medium throughput (collected filtrate mass or volume) is measured at 120 minutes from the start of the experiment. Membrane capacity is determined as a minimum area, expressed as Amin, in units of square meters (m²). The minimum area can be arbitrarily defined as the membrane area required to collect a given quantity of filtrate within a given time interval. In this case, the minimum area is defined as the filter area needed to collect or filter 1000 Liters of feed in a 4 hour time and is calculated from the flux decay curve (raw experimental volume vs time data) recorded for each device.

Figure 9A:
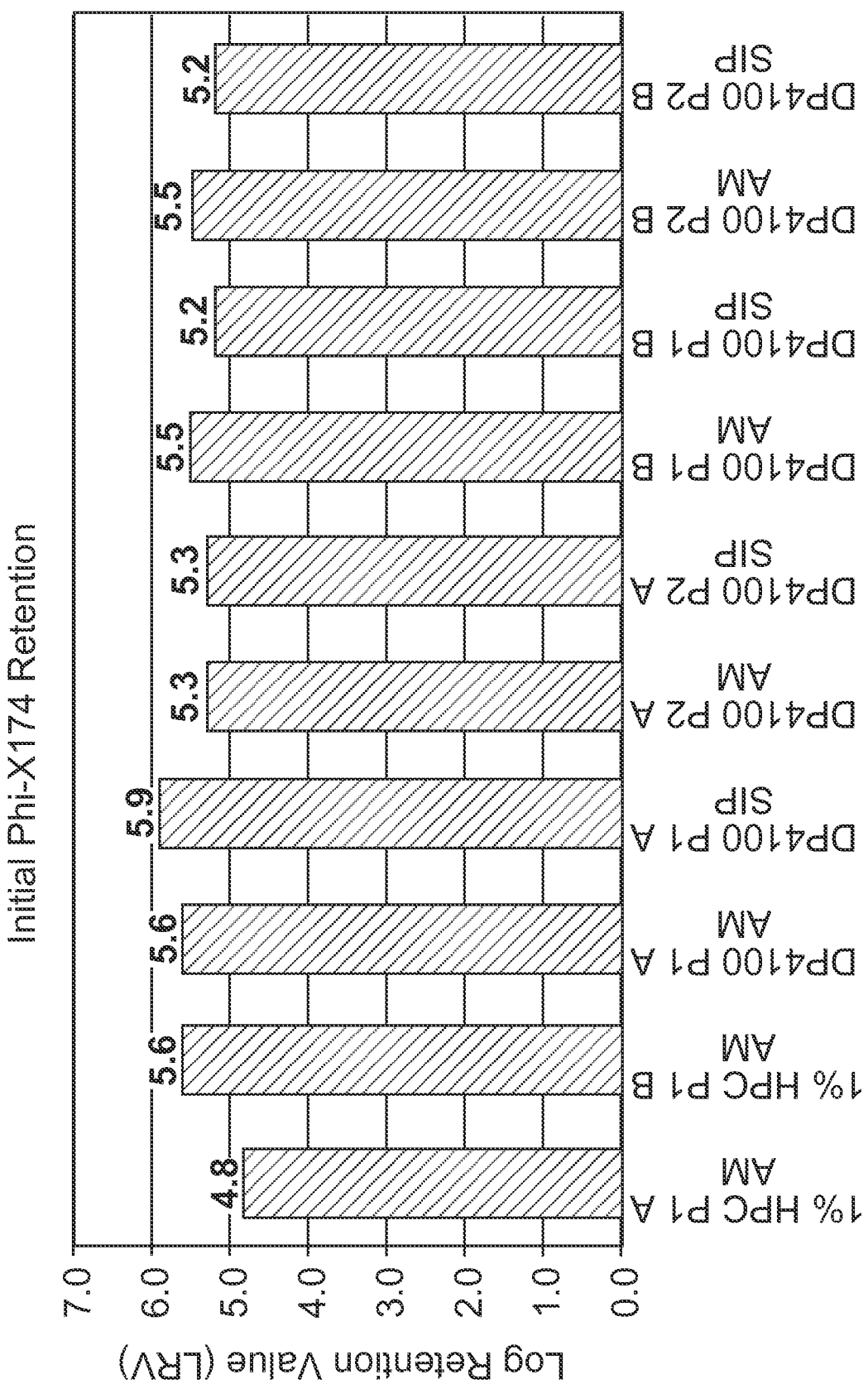
FIGS. 9a and 9b are bar graphs depicting the log retention value (LRV)Phi-X174 of various membranes before and after steam-in-place (SIP) treatment, as measured at the start of experiment (initial LRV, shown in 9a) and end of experiment (final LRV, shown in 9b). Membranes tested are cast from PES polymers from two different sources, referred to as P1 and P2 herein and are tested in duplicate (referred to as A and B). The membrane devices tested are: 1% HPC P1 as control with no thermal treatment (AM), used in duplicate (referred to as 1% HPC P1 AM A and B); modified membranes (i.e., 4.00%-DACm1.00%-PEGDA) with no thermal treatment (AM), which are as follows-DP4100P1 AM A; DP4100 P2 AM A; DP100 P2 AM A; D4 100 P1 AM B; and D4100P2 AM B; and modified membranes (i.e., 4.00%-DACm1.00%-PEGDA) with steam-in-place treatment (SIP), which are as follows-DP4100P1 SIP A; DP4100P2 SIP A; DP4100 P1 SIP B; and DP4100 P2 SIP B. The X-axis represents the various membrane devices and the Y axis represents the LRV.
Figure 9B:
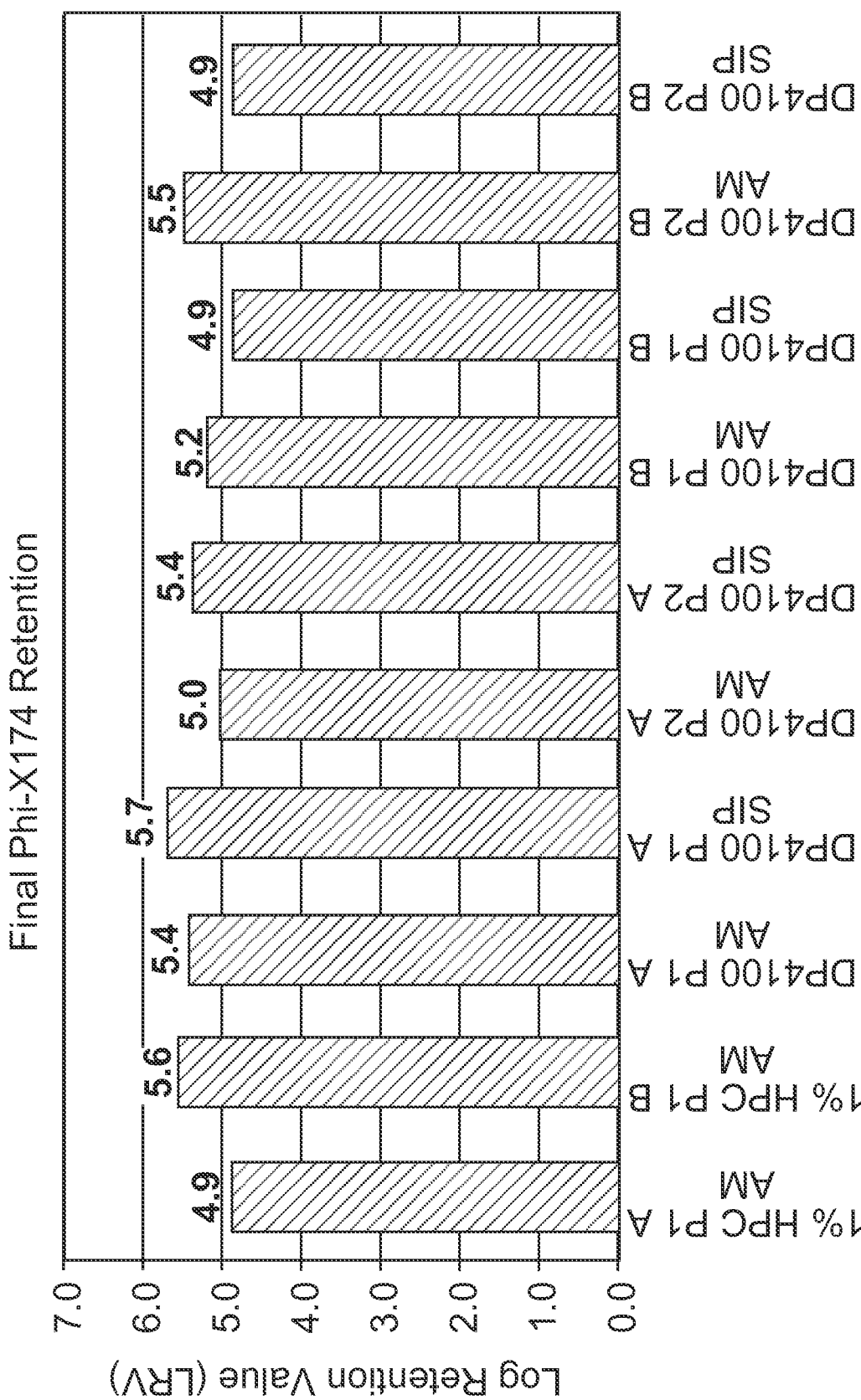

Retention is determined by spiking Phi-X174 bacteriophage (Promega Catalog No. 11041) into the feed at a titer of $2-5\times10^7$ pfu/uL (plaque-forming units per microliter). A 1 ml feed sample is secured from the feed reservoir before beginning the throughput experiment. Once the experiment is started, an initial 1 ml retention sample is secured at the outlet of each device after about one minute. Before terminating the experiment, a final 1 ml retention sample is secured at each device. When the experiment is terminated, the feed is sampled at the feed reservoir again. The feed reservoir samples are used to measure the titers and thus the viability of the phage at the start and end of the test. The filtrate samples taken at the device outlets at the initial and final points during the test are used to determine the numerical difference between the initial viable bacteriophage titer and the final viable bacteriophage titer. These differences between initial and final titers from the device outlets relative to the feed reservoir samples are used to determine the log reduction value (LRV) for each device. In general, the LRV is a measure of how effective virus removal is. Each unit log value represents a reduction in the virus titer by an order of magnitude (10×). Therefore, an LRV of 5 means that virus concentration of the filtrate is 1/100000 of the virus concentration of the feed. The initial and final retention results are depicted in FIGS. 9a and 9b, respectively. FIG. 9a presents the Initial LRV values, one for each device. FIG. 9b presents the Final LRV values, one for each device. Notably no significant change in LRV occurs after the SIP treatment, and that no significant change in LRV occurs between initial and final LRV measurements for any devices tested in this experiment. However, significant capacity improvements are observed for all DP4100 devices relative to the 1% HPC devices.

Example 6: Evaluation of Throughput Performance of DACm-Free Membranes

In a representative experiment, membranes modified with PEGDA alone (2 to 5%) are made, in order to investigate whether DACm is a necessary component to achieve the desirable throughput performance. A series of membranes are modified using PEGDA575 concentration ranging from 2% to 5% by weight in water in 1% increments. A PES membrane is used as the base membrane and a 1% hydroxypropyl cellulose (HPC) modified membrane, as previously described, is used as a control. Throughput performance testing on this membrane series is carried out using a prototype chemically-defined cell culture medium (Beta-CHO, also referred to as MX-201). The various membrane modifications are made using electron beam initiated in-situ polymerization of the PEGDA575 solution-wetted PES base membrane in order to impart increasing levels of polymer onto the membrane surface with increasing (2%, 3%, 4%, and 5%) PEGDA treatment level. The average capacity and the average permeability of each modification level (duplicate determinations) are depicted in FIG. 10.

Figure 10:
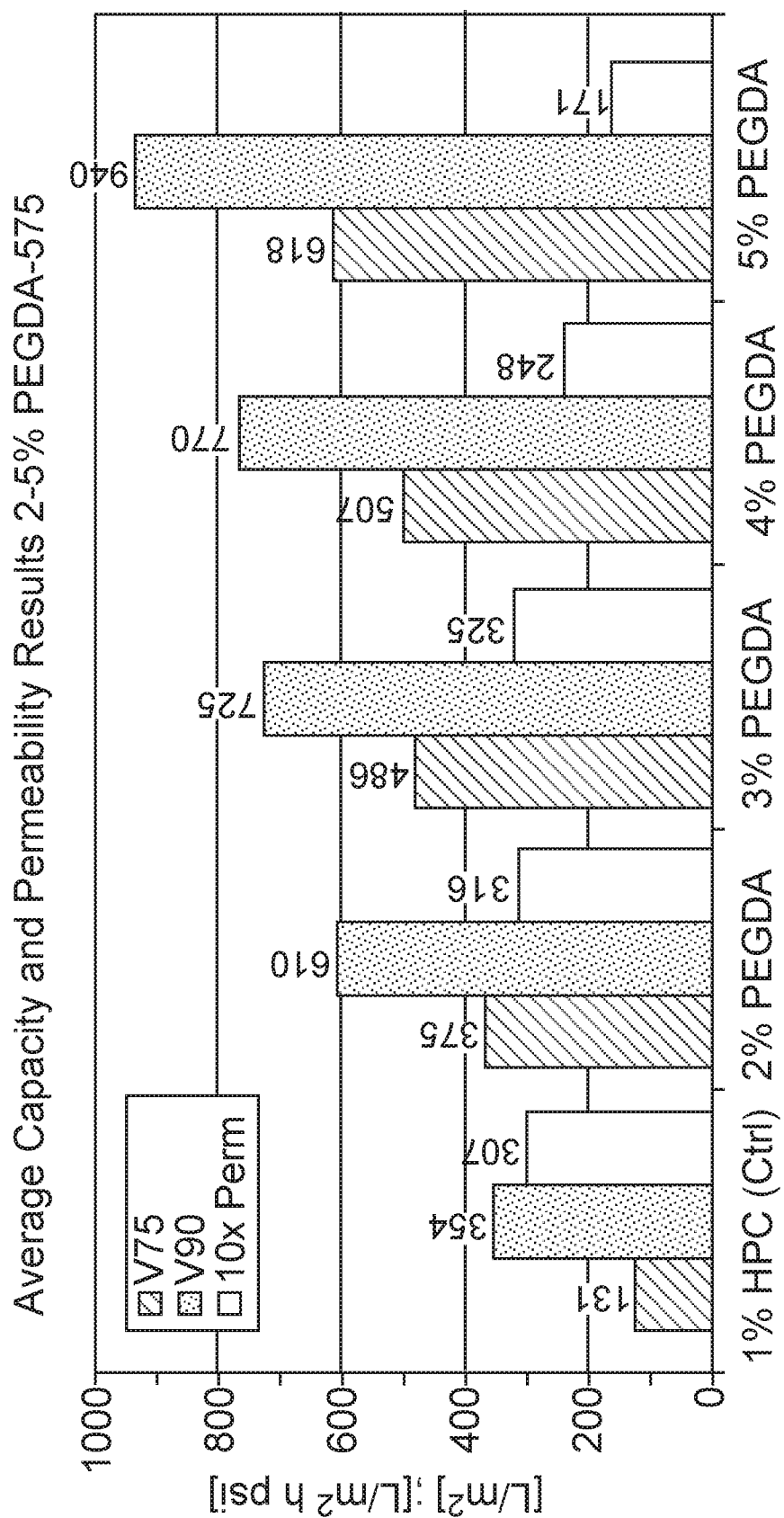
FIG. 10 is a bar graph depicting average capacity and permeability results (V75, V90 and 10× permeability) obtained with PES membranes modified with PEGDA-575 ranging from 2 to 5% using a chemically defined CHO cell culture medium. 1% HPC membrane is used as control.

As depicted in FIG. 10, capacity increases with increase in PEGDA treat level concentration, while the permeability is conversely observed to decrease.

With respect to the overall throughput performance, all PEGDA modified membranes outperformed controls by a significant factor (V75: 2.86 to 4.72; V90: 3.96 to 6.10). The performance results are compared to those summarized in Table III, where the 4% DACm-1% PEGDA575 modification resulted in performance improvement factors of 6.78 for V75 and 4.29 for V90 over 1% HPC-modified membranes. Furthermore, formulation (HEA-TEGDA, also in Table III) gave performance improvement factors over control membranes of 2.65 for V75 and 1.69 for V90.

Figure 11:
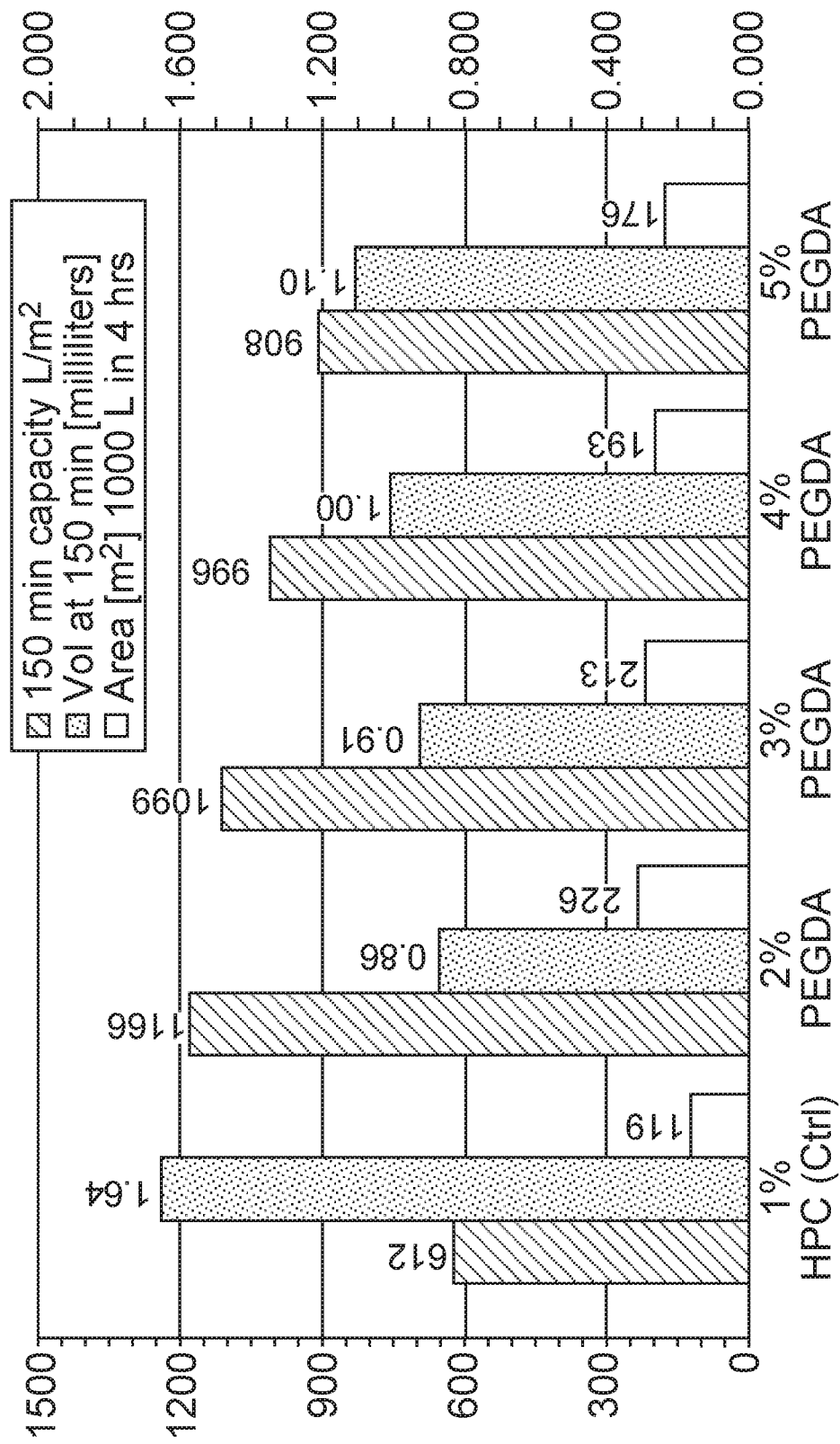
FIG. 11 is a bar graph depicting capacity of PES membranes modified with PEGDA-575 ranging from 2 to 5% and minimum area required to filter 1000 liters of medium in 4 hours. 1% HPC is used as control membrane. The left Y-axis represents the Opti-CHO filtrate volume and membrane capacity at 150 minutes and the right Y-axis represents the minimum area to filter 1000 liters in four hours.

In another representative experiment, 2%, 3%, 4%, and 5% PEGDA575 treat level membranes are prepared and tested with Life Technologies CD Opti-CHO chemically-defined cell culture medium. Again the throughput performance is observed to be improved over the 1% HPC control membrane. However, performance continues to decrease with increasing PEGDA treat level. This is depicted FIG. 11. In FIG. 11, capacity is measured in terms of Amin, which in this case is defined as the minimum membrane area (in units of $m^2$) that is required to process 1000 Liters of media in a 4 hour period. Notably, an inverse relationship of Amin to the amount of filtrate collected over the first 150 minutes of the experiment is observed. Therefore, a lower Amin corresponds to higher capacity. Due to the seemingly opposing performance trends of these membranes with respect to the two different media streams, membrane performance was further evaluated using multiple feedstreams. It appears that the membrane performance results using the MX-201 medium shown in FIG. 10 improve with increasing PEGDA treat level while the membrane performance results using the CD Opti-CHO results shown in FIG. 11 are diminished with the same increase in PEGDA treat level. It is noted that the MX-201 medium is more fouling than the Opti-CHO medium. As a result, the device performance using the MX-201 medium is less affected by the permeability and more by the fouling by the medium. Whereas, the Opti-CHO medium is less fouling, therefore, the device performance is more dependent on the permeability than the effect of fouling by the medium.

Example 7: Performance Evaluation of DACm-Free Membranes and of DACm-PEGDA Membranes Using Multiple Feedstreams Because of the attractive performance trends of membranes without DACm, in yet another representative experiment, a series of membranes modified with PEGDA alone or with DACm and PEGDA are investigated for throughput performance One control consists of the hydrophobic PES virus membrane with a 1% HPC surface modification, and the second control membrane consisted of a PES virus membrane modified with 4% DACm and 1% PEGDA575. The second control is made using a different hydrophobic membrane lot compared to the other membranes in this experiment. The three remaining membranes include a 1% PEGDA modification, a 1% PEGDA and 1% DACm modification, and finally a 1% PEGDA575 and 4% DACm modification. Three data sets were collected with this membrane set, one using each of the following feedstreams: 1) Commercially available chemically-defined CHO cell culture medium, Life Technologies CD Opti-CHO; 2) Commercially available chemically-defined CHO cell culture medium, EMD Cellvento 200; and, 3) Experimentally devised feedstream, Dulbecco's Modified Eagle Medium spiked with 2 g/Liter of Pluronic.

Figure 12:
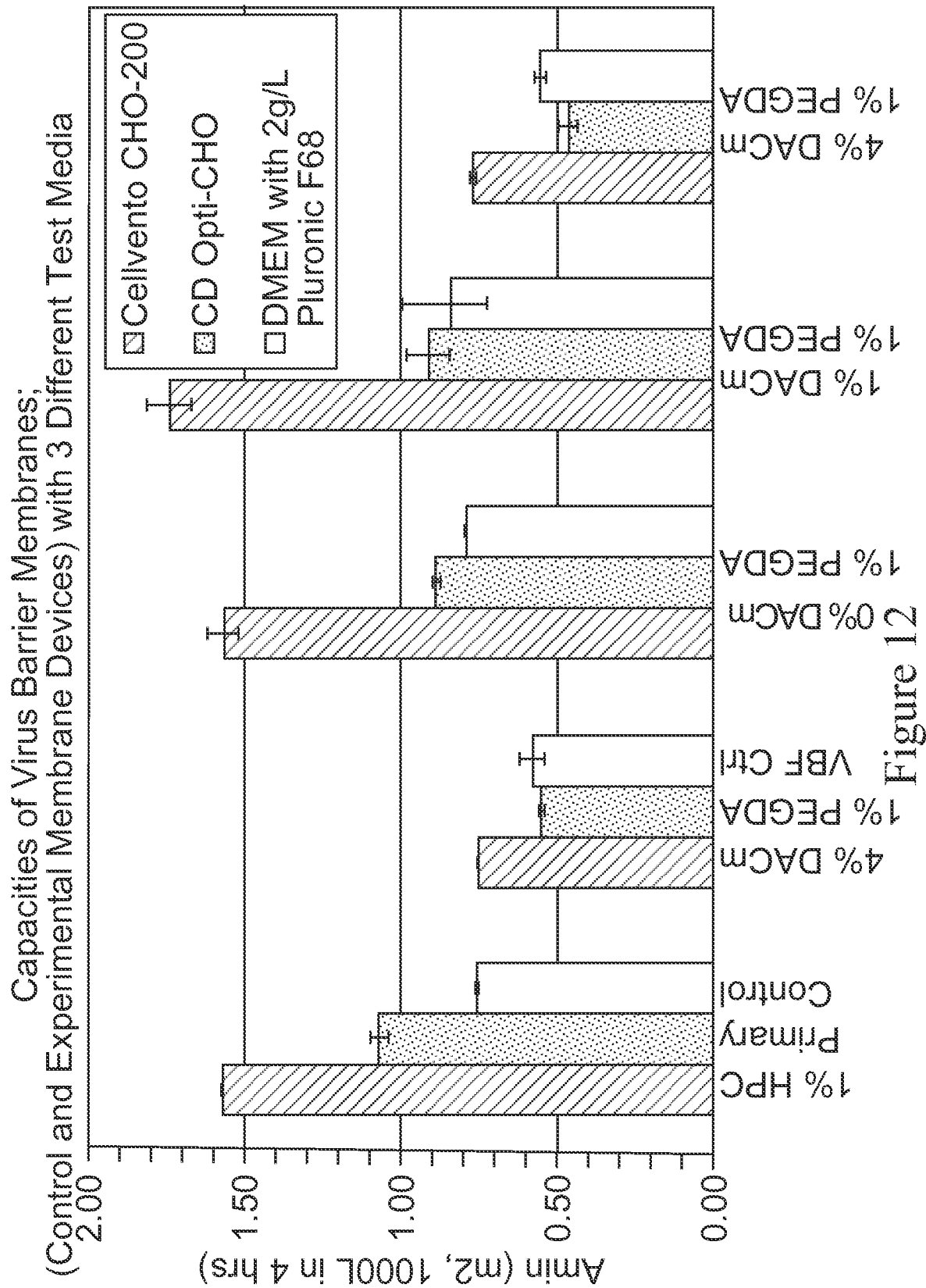
FIG. 12 is a bar graph depicting capacities of various membranes using 3 different chemically defined media (i.e., Cellvento CHO-200, CD Opti-CHO and DMEM spiked with 2 g/L Pluronic F68). The membranes tested are: PES modified with 1% HPC (used as control); PES membrane modified with 4% DACm-1% PEGDA; PES membrane modified with 0% DACm-1% PEGDA; PES membrane modified with 1% DACm-1% PEGDA; and PES membrane modified with 4% DACm-1% PEGDA. The X-axis represents the type of membrane and the Y-axis represents Amin, which is the minimum area required to filter 1000 liters of medium in 4 hours.

FIG. 12 depicts the comparative throughput performance various membranes. The surface modifications include (from left to right in the figure): control membrane modified with 1% HPC; membrane modified with the 4% DACm and 1% PEGDA575; membrane modified with only 1% PEGDA575; membrane modified with 1% DACm and 1%

PEGDA575; and membrane modified with 4% DACm and 1% PEGDA575. It is observed that with the CD Opti-CHO medium, which is considered a lower fouling medium, the low DACm and no-DACm surface modified membranes perform relatively well and very similar to the 2% PEGDA membrane shown in FIG. 11. In the case of the higher fouling Cellvento-200 medium, only the higher-level DACm surface modifications perform well. This demonstrates that the higher DACm-level surface modifications provide improved throughput performance for the widest set of feedstreams tested.

The specification is most thoroughly understood in light of the teachings of the references cited within the specification which are hereby incorporated by reference. The embodiments within the specification provide an illustration of embodiments and should not be construed as limiting in scope. The skilled artisan (practitioner) readily recognizes that many other embodiments are encompassed by this disclosure. All publications and reference materials are incorporated by reference in their entirety. To the extent that the material incorporated by reference contradicts or is inconsistent with the present specification, the present specification will supercede any such material. The citation of any references herein is not an admission that such references are prior art.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the embodiments disclosed herein. Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the disclosure being indicated by the following claims.

What is claimed is:

1. An asymmetric, porous polyethersulfone membrane having a surface modified with a polymer consisting essentially of randomly arranged and crosslinked monomers of diacetone acrylamide and a non-acrylamide cross-linkable difunctional monomer, wherein the non-acrylamide cross-linkable difunctional monomer is polyethylene glycol diacrylate.

2. The membrane of claim 1, wherein the polymer is directly coated on the surface of the porous membrane using an energy source.

3. The membrane of claim 2, wherein the energy source is selected from the group consisting of heat, electron beam, ultraviolet light and gamma radiation.

* * * * *